(12) United States Patent
Haidekker

(10) Patent No.: US 7,517,695 B2
(45) Date of Patent: *Apr. 14, 2009

(54) LOCAL FLOW AND SHEAR STRESS SENSOR BASED ON MOLECULAR ROTORS

(75) Inventor: Mark A. Haidekker, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 830 days.

This patent is subject to a terminal disclaimer.

(21) Appl. No.: 11/039,357

(22) Filed: Jan. 20, 2005

(65) Prior Publication Data

US 2006/0079001 A1    Apr. 13, 2006

Related U.S. Application Data

(60) Provisional application No. 60/537,680, filed on Jan. 20, 2004.

(51) Int. Cl.
  *G01N 21/64*    (2006.01)
  *G01N 33/44*    (2006.01)

(52) U.S. Cl. .......... 436/172; 422/82.05; 422/82.06; 422/82.07; 422/82.08; 436/2; 436/85

(58) Field of Classification Search ... 422/82.05–82.08; 436/2, 172, 85
See application file for complete search history.

(56) References Cited

U.S. PATENT DOCUMENTS 4,582,809 A * 4/1986 Block et al. ............ 436/527
4,980,278 A * 12/1990 Yamada et al. ......... 435/7.92
5,384,079 A *  1/1995 Bur et al. ................. 264/21
2003/0077649 A1 * 4/2003 Cho et al. .................. 435/6
2006/0084177 A1 * 4/2006 Haidekker et al. ...... 436/148

OTHER PUBLICATIONS

Carre, M. C. et al, Journal of Fluorescence 1998, 8, 53-57.*
Haidekker, M. A. et al, SPIE 2000, 3921, 101-112.*
Haidekker, M. A. et al, Chemistry & Biology 2001, 8, 123-131.*
Mallipattu, S. K. et al, Journal of Comparative Physiology A 2002, 188, 409-416.*
Haidekker, M. A. et al, American Journal of Physiology 2002, 282, H1609-H1614.*
Haidekker, M. A. et al, Bioorganic & Medicinal Chemistry 2002, 10, 3627-3636.*
Haidekker et al. "Sensing of Flow and Shear Stress Using Fluorescent Molecular Rotors", Sensor Letters 2005, vol. 3, 42-48, Copyright 2005 American Scientific Publishers.

* cited by examiner

*Primary Examiner*—Arlen Soderquist
(74) *Attorney, Agent, or Firm*—Greer, Burns & Crain, Ltd.

(57) ABSTRACT

A method for detecting local shear stress values using molecular rotors that allows for an extremely sensitive determination of a shear stress field or a flow field, even at very low flow rates. In one embodiment, molecular rotors may be adhered to a fiber optic probe or other solid surface, and the fluorescence emission of those molecular rotors may be probed at a location of the fiber optic probe tip or other solid surface. In another preferred embodiment, rotors may be adhered to another solid surface, such as any glass or polymer substrate that may be pre-functionalized (e.g., quartz, polystyrene or silicate glass) to create a probe that may then be used for in vivo as well as in vitro viscosity measurements. In another embodiment, molecular rotors may be dissolved in a target solution, and emission intensity obtained by one of several techniques.

29 Claims, 22 Drawing Sheets

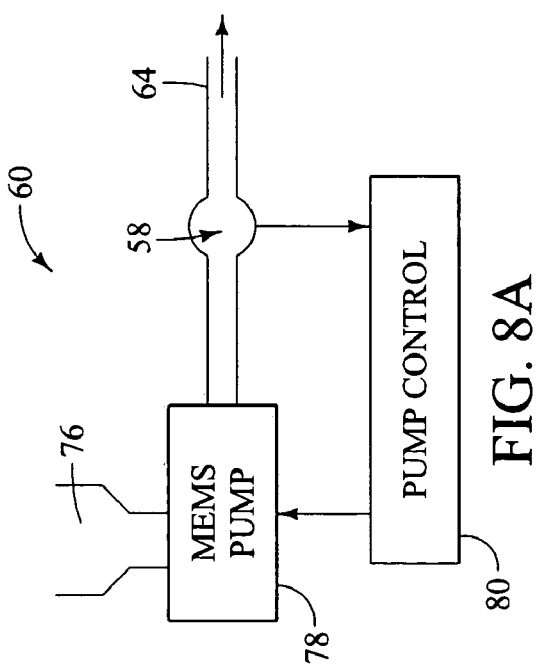
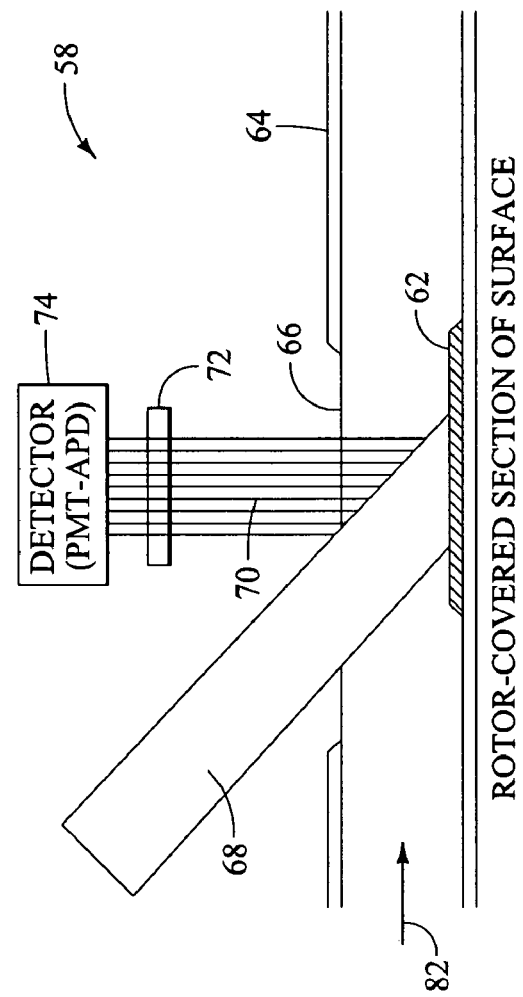
FIG. 8A
FIG. 8B

LOCAL FLOW AND SHEAR STRESS SENSOR BASED ON MOLECULAR ROTORS

CROSS-REFERENCE TO RELATED APPLICATION

Pursuant to 35 U.S.C. §119(e), this application is entitled to the benefit of U.S. Provisional Application Ser. No. 60/537,680, filed Jan. 20, 2004.

STATEMENT OF GOVERNMENT INTEREST

This invention was made with Government support under Contract Number NIH 1R21 RR018399 awarded by the National Institutes of Health. The Government has certain rights in the invention.

FIELD OF THE INVENTION

A field of the invention is biofluid analysis. Another field of the invention is micro-fluidics, including industrial applications for monitoring flow in microchannels. Flow may also be monitored in larger channels. The invention is particularly suitable for low-flow regimes, and may be used in closed-loop flow control and verification of computed flow dynamics. Other exemplary fields of the invention include medical diagnosis, medical test systems, and medical laboratory processes.

BACKGROUND OF THE INVENTION

Molecular rotors are known for their viscosity-sensitive fluorescence quantum yield. This group of fluorescent dyes consists of two molecular subunits (an electron donor group and an electron acceptor group) that are linked through a single bond. Intramolecular rotation or twisting around that single bond is possible. This rotation, a thermally-induced effect, leads to non-fluorescent de-excitation. Inhibition of this intramolecular rotation, typically seen in solvents with high viscosity, causes a shift towards radiative relaxation. As a consequence, fluorescence quantum yield increases in media with increasing viscosity.

A novel effect has been observed that molecular rotors with a polar group dissolved in a polar solvent, exhibit a strong increase in quantum yield when exposed to solvent velocity gradients. This effect allows designing of fluorescence-based shear stress sensors in arbitrary flow fields.

The observation of velocity fields is a difficult task. Often, high-speed microscope imaging is used to obtain time-lapse frames of microspheres suspended in the fluid. Their displacement between frames allows the computation of the flow field. Additional methods include Doppler ultrasound, laser-Doppler velocimetry, and imaging methods based on magnetic resonance. All methods are fairly complex and highly susceptible to noise, particularly at low flow rates. In addition, MRI and ultrasound methods suffer from low spatial resolution, and imaging equipment (especially MRI) is prohibitively expensive.

Shear stress, the product of fluid viscosity and shear rate, is impossible to obtain by noninvasive imaging-based methods. Mechanical methods can be devised to obtain information on the drag forces of a viscous fluid, but they disturb the flow field and require a complex mechanical setup involving bodies susceptible to drag attached to the base through elastic linkers. These methods are not established and are limited to laboratory geometries.

SUMMARY OF THE INVENTION

The instant invention is related to a method for detecting local shear stress values using molecular rotors. Embodiments of the invention allow for an extremely sensitive determination of a shear stress field or a flow field, even at very low flow rates. In a first preferred embodiment, predetermined molecular rotors may be adhered to a fiber optic probe or other solid surface, and the fluorescence emission of those molecular rotors may be probed at a location of the fiber optic probe tip or other solid surface. For example, where molecular rotors are adhered to a fiber optic probe tip, the fiber optic probe may be inserted into a tube or blood vessel to measure a shear stress field either in vivo or in vitro. In another preferred embodiment, rotors may be adhered to another solid surface, such as any glass or polymer substrate that may be pre-functionalized (e.g., quartz, polystyrene or silicate glass) to create a probe that may then be used for in vivo as well as in vitro viscosity measurements. In another preferred embodiment, predetermined molecular rotors may be dissolved in a target solution, and emission intensity obtained by one of several techniques.

DESCRIPTION OF THE DRAWINGS

FIGS. 8A and 8B are schematic diagrams illustrating a rotor-based flow sensor element and a closed-loop flow control system in accordance with an embodiment of the invention;

DETAILED DESCRIPTION OF THE INVENTION

Figure 1B:
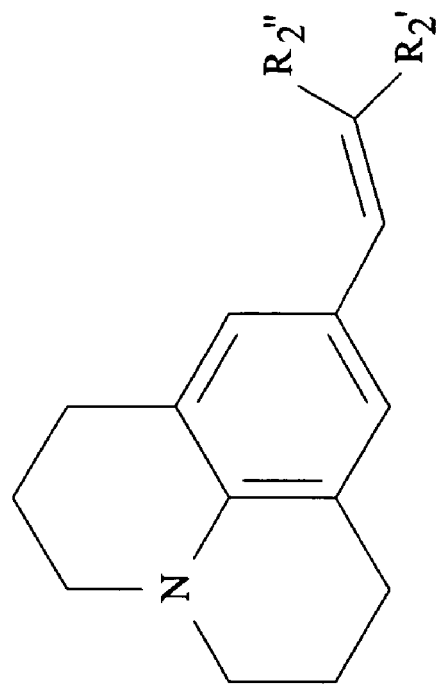
FIGS. 1A, 1B, 1C, 1D, 1E, and 1F illustrate generic structures of exemplary rotors.
Figure 1A:
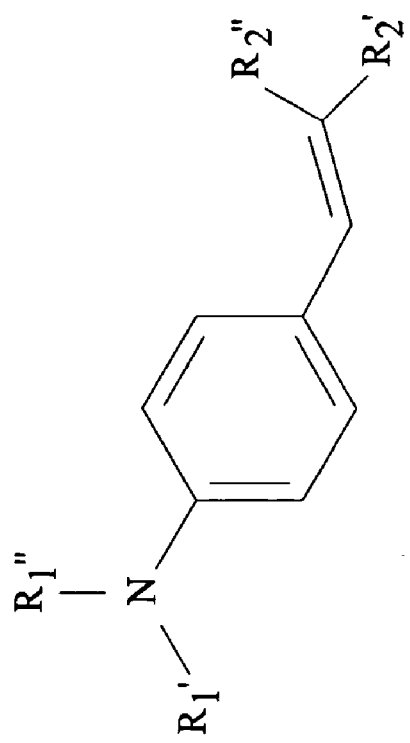
Figure 1C:
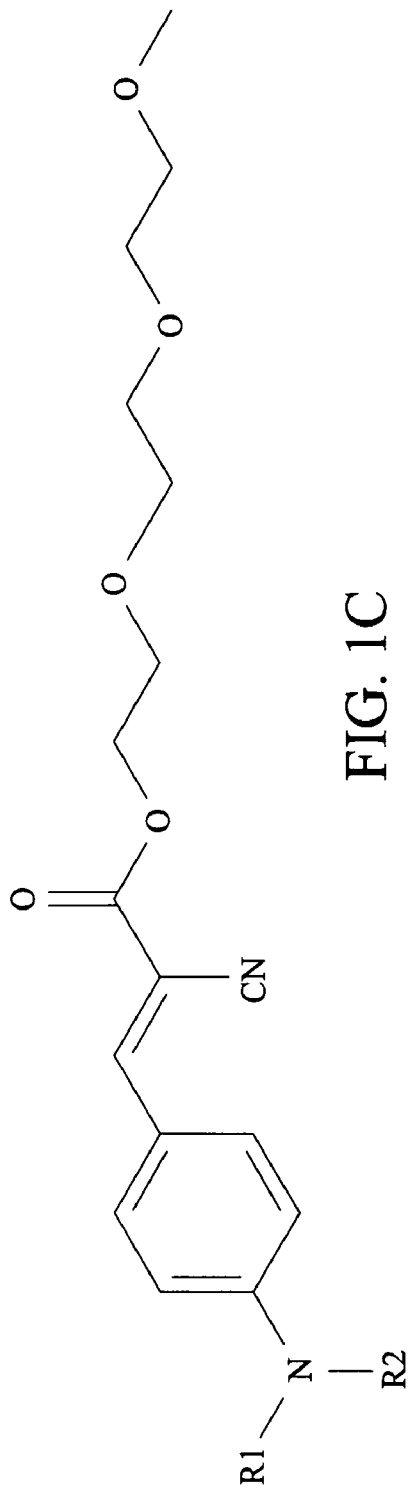
Figure 1D:
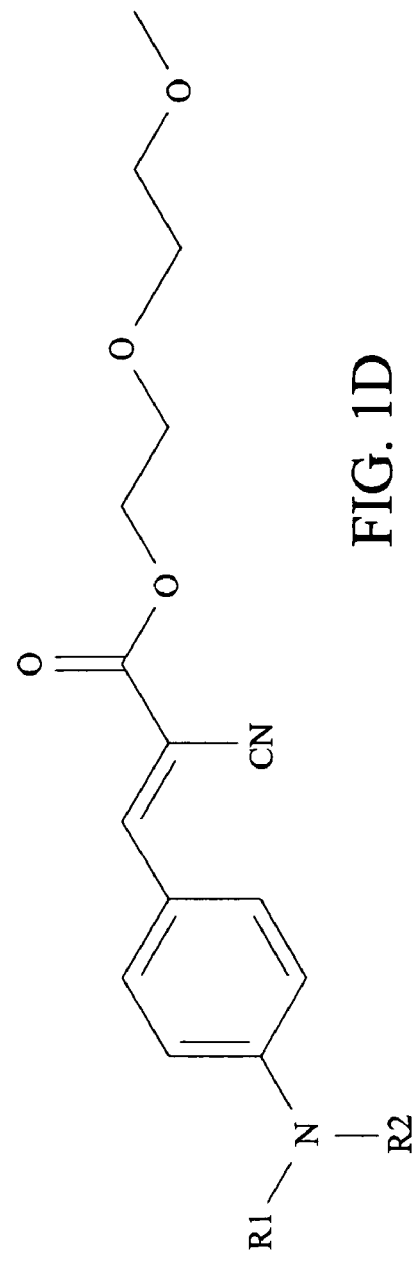
Figure 1E:
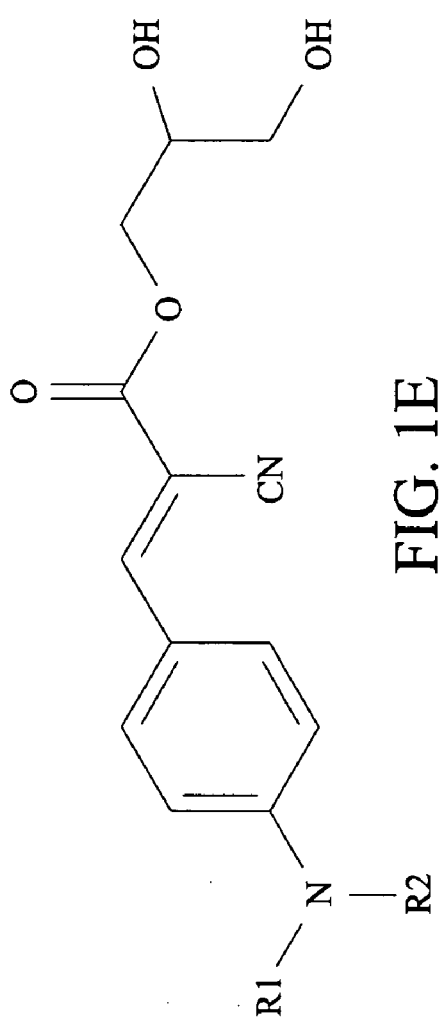
Figure 1F:
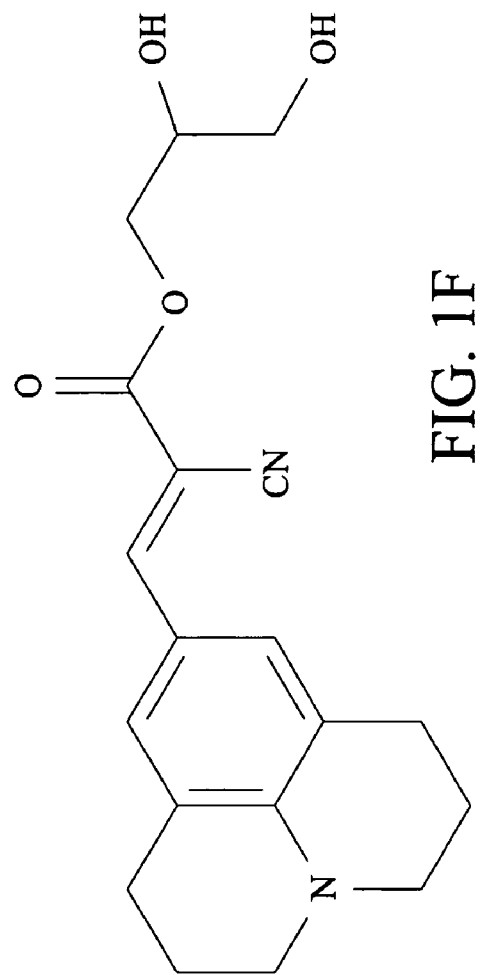

Shear stress is proportional to a flow gradient, and thus is also proportional to the absolute magnitude of flow and average flow rate. Embodiments of the invention allow for an extremely sensitive determination of a shear stress field or a flow field, even at very low flow rates. In a first preferred embodiment, predetermined molecular rotors may be adhered to a fiber optic probe or other solid surface, and the fluorescence emission of those molecular rotors may be probed at a location of the fiber optic probe tip or other solid surface, either in vivo or in vitro.

For example, where molecular rotors are adhered to a fiber optic probe tip, the fiber optic probe may be inserted into a tube or blood vessel to measure a shear stress field either in vivo or in vitro. In another preferred embodiment, rotors may be adhered to another solid surface, such as any glass or polymer substrate that may be pre-functionalized (e.g., quartz, polystyrene or silicate glass) to create a probe that may then be used for in vivo as well as in vitro viscosity measurements. In another preferred embodiment, predetermined molecular rotors may be dissolved in a target solution, and emission intensity obtained by one of several techniques. Those techniques include single bulk emission value, which is related to average shear stress by fluoroscopy techniques, or a projection of intensity by a moving detector or a CCD or similar imaging element, or multiple projections combined with rotations, which allow for the three-dimensional intensity distribution to be reconstructed using tomography methods. Preferred embodiments promote a highly accurate measurement of shear distribution in a volume of interest.

A Newtonian fluid will exhibit a linear relationship between shear rate and shear stress, where shear stress is a product of fluid viscosity and shear rate. Thus, in a Newtonian fluid, viscosity is independent of the applied shear conditions. In contrast, a non-Newtonian fluid does not exhibit such a relationship. The most common form of non-Newtonian flow behavior is shear-thinning or pseudoplasticity, which is a decrease in viscosity with increasing shear, and is seen in most complex fluids, e.g. colloids, gels and solutions. Biofluids are typically non-Newtonian fluids that include large proteins that may appear to alter viscosity. When biofluids are at rest, macromolecules form non-covalently bound aggregates. Under flow, those molecular aggregates break apart, resulting in a reduction of fluid viscosity.

In both Newtonian and non-Newtonian fluids, shear stress is more determinative of viscosity, but is more difficult to measure than flow or shear rate. Additionally, shear stress appears to be of unique interest in the human circulatory system, insofar as increased shear stress appears to have a positive correlation with some circulatory diseases, such as arteriosclerosis. Accordingly, embodiments of the instant invention therefore provide novel systems and methods for gathering information about shear stress in fluid systems using predetermined molecular rotors. Thus, embodiments of the invention have vast potential for applications including clinical research, namely monitoring of local blood flow and shear stress in blood vessels in real time over the cardiac cycle, as well as in exploration of capillary blood flow. Industrial applications include such things as monitoring of flow in microfluidics, microchannels, or medium-sized tubes or channels. Still other applications include flow measurement, particularly in the low-flow regime, closed-loop flow control, detection of imperfections that cause disturbed flow, and verification of computed fluid dynamic models.

Generally, molecular rotors exhibit viscosity sensitivity because intramolecular rotation rate depends on the viscosity of the solvent. However, some molecular rotors exhibit markedly increased emission intensity at relatively low shear rates, and the emission primarily depends upon shear stress rather than shear rate. For example, significant intensity increases have been observed at flow rates of 0.6 mm/s, corresponding to 0.25 ml/min in a 4 mm diameter tube. Thus, embodiments of the instant invention provide an extremely sensitive device and method for measuring relatively low shear rates, and include any of those specific molecular rotors having hydrophilic head groups and additionally demonstrate a shear sensitivity by exhibiting an elevated emission intensity in fluids under shear. Thus, embodiments of the invention are particularly useful and advantageous in flow measurement and flow monitoring in the low-flow regime. One example is a steady low-volume drug delivery from pump systems such as osmotic pumps. Another application of the invention includes a MEMS pump control, which is otherwise difficult to monitor. The invention overcomes the difficulty associated with a MEMS pump control by providing for for (1) measurement of pump flow, (2) observation of the flow distribution inside the pump mechanism itself to optimize its performance, and (3) the use of rotor-based flow sensing to perform closed loop control.

For example, FIGS. 1A through 1F illustrate generic examples of molecular rotors that may be used with the invention, while FIGS. 2A through 2G illustrate several specific exemplary rotors, which are, respectively, 9-(2-carboxy-2-cyanovinyl)-julolidine (CCVJ); 9-(2-carboxy-2-cyanovinyl)-julolidine triethyleneglycol ester (CCJV-TEG); 2-Cyano-3-(4-dimethylamino-phenyl)-acrylic acid methyl ester (DMCJ); 2-Cyano-3-(4-dibutylamino-phenyl)-acrylic acid methyl ester (SC1-20A); 2-Cyano-3-(4-diethylamino-phenyl)-acrylic acid methyl ester (SC1-40B); 2-Cyano-3-(4-diethylamino-2-pentyloxy-phenyl)-acrylic acid methyl ester (SC1-30B); and 2-Cyano-3-(2-cyclohexylmethoxy-4-diethylamino-phenyl)-acrylic acid methyl ester (SC1-31B). Preferably, the molecular rotors included in both the first and second preferred embodiments include those molecular rotors having functional groups R2' and R2" that act both as electron acceptors and as polar groups. For example, exemplary functional groups are —OH, —COOH, —CH2—CH$_2$—O—CH$_3$. If at least one of R2' or R2" are one of the exemplary functional groups, the shear sensitive molecular rotor is complete. The other R2 may be used as an attachment or recognition unit.

Fiber-Optic Based Shear Sensor with Molecular Rotors in Solution for In Vitro Applications:

For some in vitro applications, a hydrophilic molecular rotor, such as CCVJ, is dissolved in the fluid to be observed at a predetermined concentration, such as between 1 µM and 30 µM. A tip of a fiber optic probe is then inserted into the flow channel, which may be a tube, microchannel or other vessel. The fiber optic probe is coupled to a fluorometer. The fiber can either act as a light guide for both excitation and emission light or, in specific environments, act as a guide for emission light only when external excitation light is provided. Using a cannula, the tip of the fiber optic probe is exposed to the fluid in motion. Due to the geometry of the tip, flow perturbation is minimal if the tip points upstream. Depending on the position of the tip relative to the vessel wall, shear stress values in the different regions of flow may be obtained. Emission light is preferably only captured from a layer of sub-micron thickness above the tip surface. The emission intensity may then be used to draw conclusions on the shear stress.

Figure 3B:
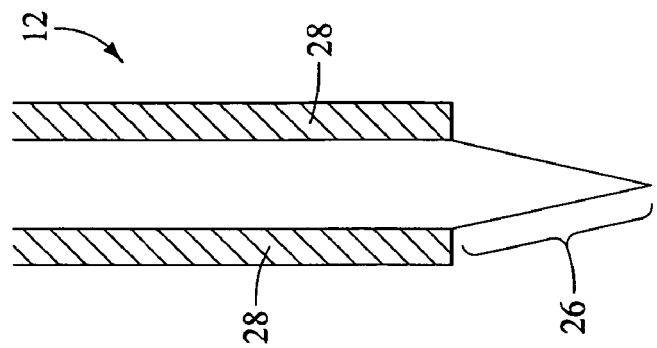
FIGS. 3A and 3B are schematic diagrams of the fiber optic-based shear stress sensor and a fiber optic tip.
Figure 3A:
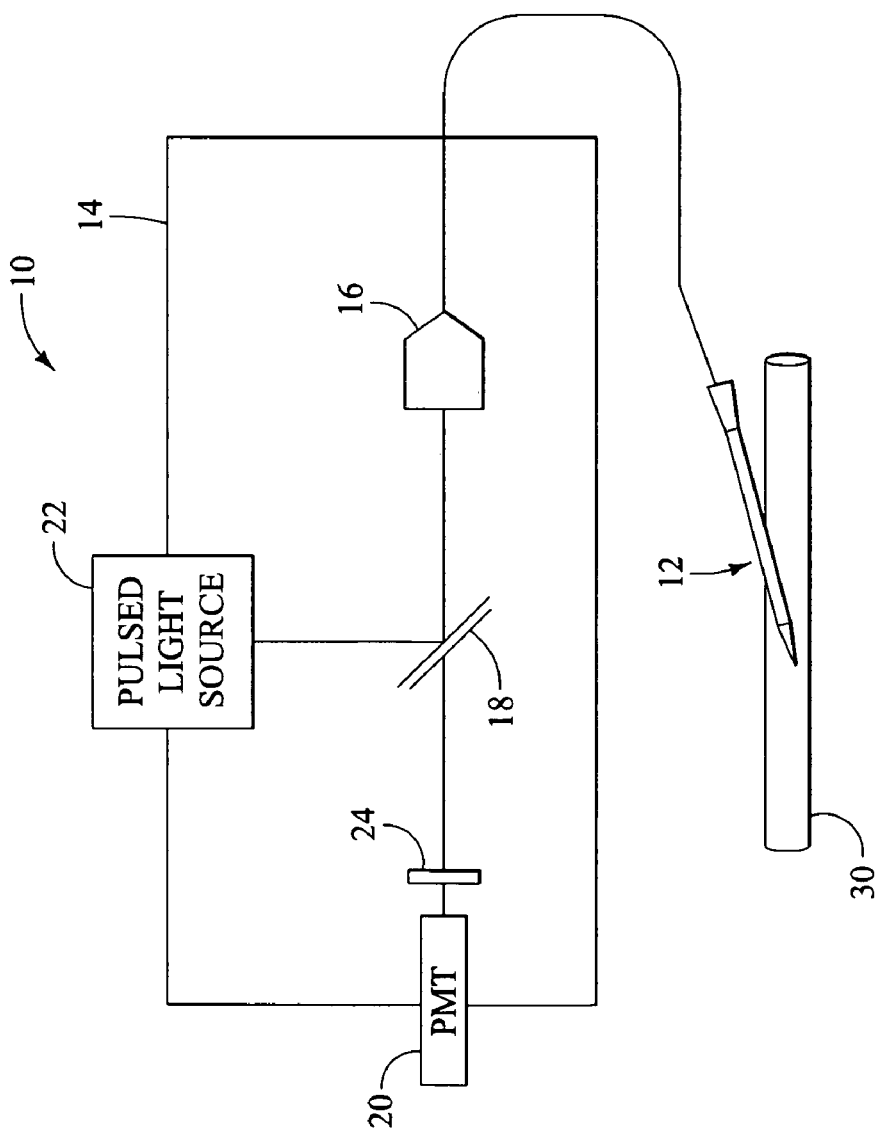

More specifically, as illustrated in FIGS. 3A and 3B, a beamsplitter assembly, indicated generally at 10, is used to couple excitation light into a fiber optic probe, designated generally at 12, and to collect emission light. The fiber optic probe 12 is preferably coupled to a light-proof encasing 14, which houses a fiberoptic coupling device 16 and a dichroic mirror 18. A photo-multiplier tube 20 is also provided, as is a pulsed light source 22. A longpass filter 24 is also preferably provided. The dichroic mirror 18 is used to direct blue light from a pulsed light source 16 onto the dichroic mirror and to reflect the blue light into the fiber optic probe 12. At a tip 26 of the fiber optic probe 12, the excitation evanescent wave excites the rotors in the fluid close to the surface of the tip. The remainder of the fiber optic probe is preferably enclosed in a polymer coating or plastic cover 28. The tip 26 is then exposed to a flow channel 30, such as a tube or vessel, in which molecular rotors have been dissolved. As the emission light, which is the non-reflecting wavelength of the dichroic mirror 18, exits the fiber inside the measurement device, it passes the dichroic mirror. Scattered or otherwise leaked excitation light is further filtered with the longpass filter 24 positioned in front of the detector (photomultiplier tube, or PMT). The detector then quantitatively determines emission intensity.

Fiber Optic-Based Shear Sensor with Immobilized Molecular Motors:

For some in vivo applications, molecular rotors can be attached to the surface of a fiber optic tip, other glass surfaces such as those of a cuvette, or microfluidic channels. Briefly, for purposes of illustration, one possible immobilization process would be immobilizing molecular rotors on a tip of a fiber optic probe and includes the following steps:

(a) etch a new tip on the fiber optic with hydrofluoric acid 40% solution, approximately 4 hours total, rinse in distilled water. Peel away the polymer coating to expose the tip using a razor blade and remove the cladding.

(b) wash tip in hydrochloric acid and methanol, then in sulfuric acid. Rinse and dry.

(c) sonicate tip for 6 to 8 minutes in 5% solution (v/v) of 3-aminopropyl-triethoxysilane (ABS from Signam cat no. A-3646) in absolute ethanol.

(d) bake the fiber tip for 1 minute at 120 degrees C.

(e) prepare working solution of CCVJ-NHS in 50 MM sodium bicarbonate solution pH 8.5, the final concentration of dye is 0.1 µg/µl with 10% DMSO present.

(f) incubate the tip of the fiber optic in the working solution of CCVJ-NHS for at least 1 hour. Sonicate in DMSO to remove excess dye.

While this embodiment is generally illustrated in FIGS. 3A and 3B in connection with in vitro applications, when the molecular rotors are adhered to the fiber optic probe tip, the fluid under observation does not need to contain the rotor dye itself. This leads to many potential applications in living organisms or industrial monitoring processes.

Figure 4:
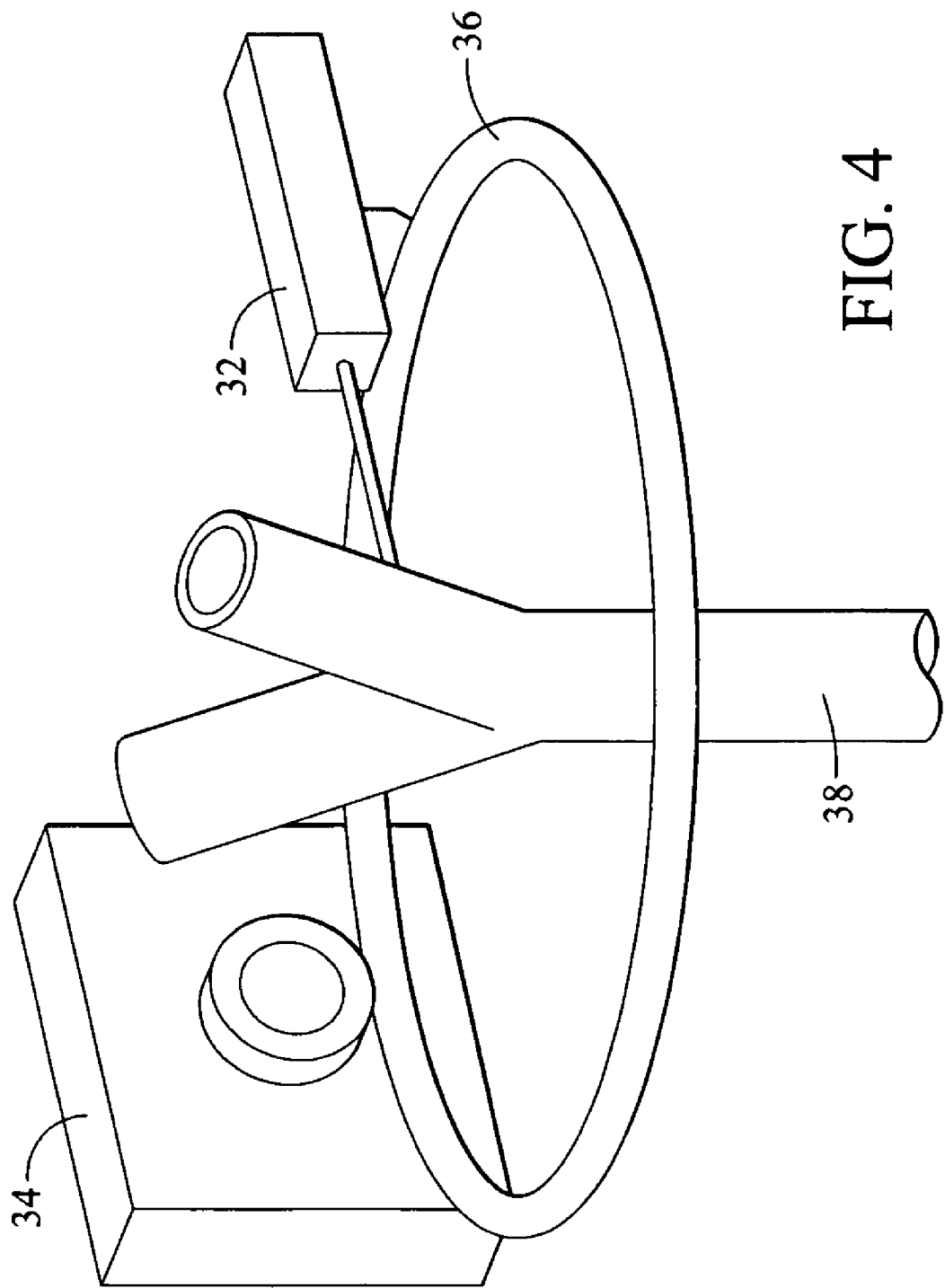
FIG. 4 is a shear field tomography system in accordance with an embodiment of the invention.

Tomography-Based Measurement of the Shear Field:

As illustrated in FIG. 4, in another preferred in vitro embodiment, reconstruction of the source density of photon emission may be accomplished by tomographical methods. This type of reconstruction is possible both in turbid and clear media and is known as fluorescence optical tomography. This method can be combined with a moving fluid field to obtain the shear stress distribution in the volume under observation.

More particularly, an exciter-detector system rotates around a sample to be observed. A specified molecular rotor is dissolved in the sample, which is then excited in a defined manner by a laser and the emission profile is acquired either by a CCD camera (non-diffusive media) or a circular detector system (diffusive media), or other suitable emission detector system. FIG. 4 illustrates an excitation light source 32 and a camera 34, which are mounted on a gantry 36 that allow it to rotate around the sample 38. A filter prevents excitation light from reaching the camera. As a result, several projections at different angles can be obtained that allow the reconstruction of the intensity distribution inside the sample A shear tomography device according to this embodiment is particularly advantageous in systems where the flow profile needs to be determined experimentally rather than by numerical stimulation. It can also be used to experimentally verify computational results. Using fast acquisition techniques, critical flow and shear behavior can be observed in relation to disease, with a typical example being the growth of atherosclerotic plaques in oscillating flow regions such as the carotid bifurcation.

Figure 5:
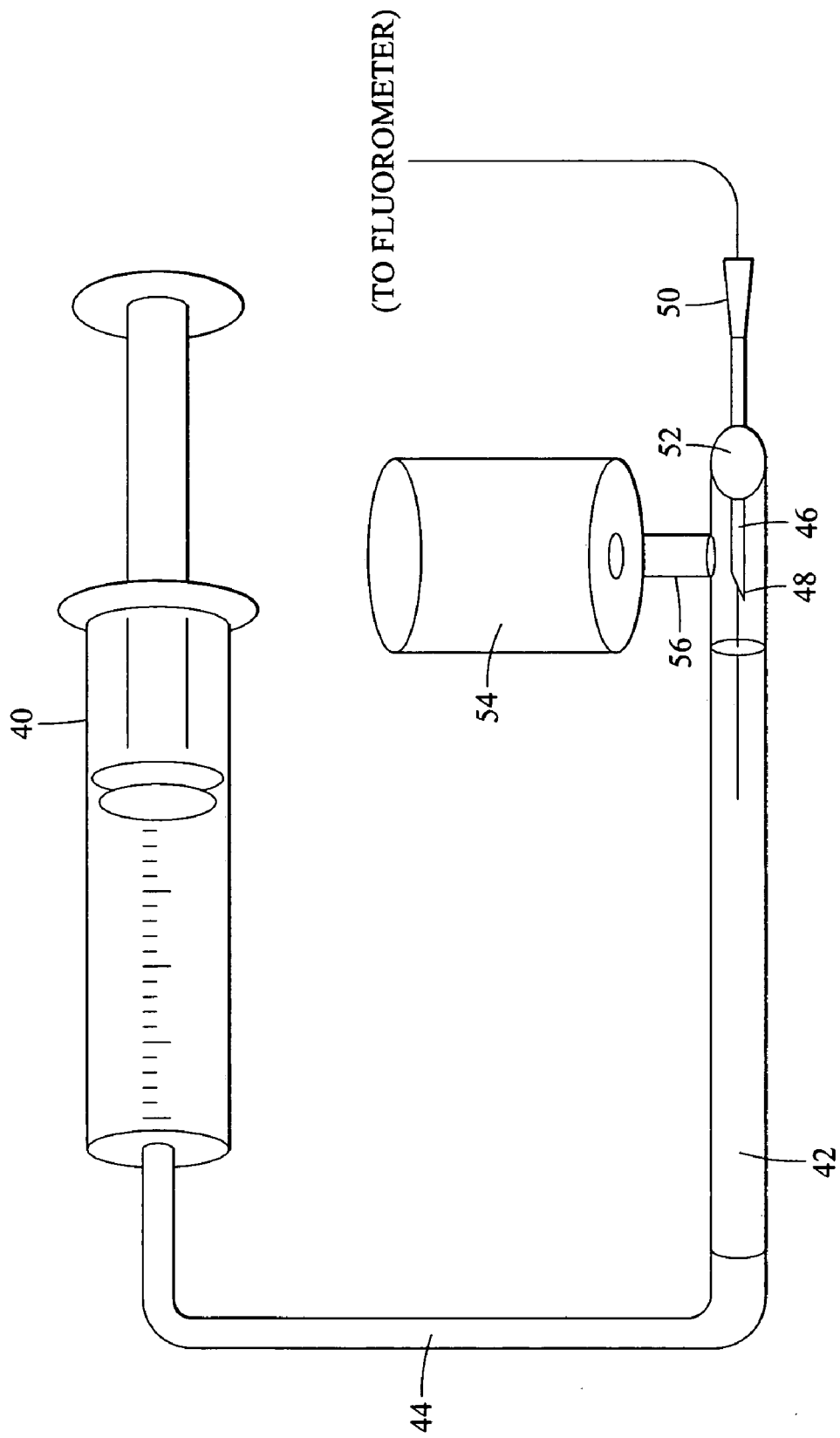
FIG. 5 is a shear apparatus to demonstrate the shear dependent intensity increase of a fluorescent molecular rotor, 9-(2-carboxy-2-cyanovinyl)-julolidine, (CCVJ), in solution.

To demonstrate the shear dependent intensity increase of a fluorescent molecular rotor, 9-(2-carboxy-2-cyanovinyl)-julolidine, (CCVJ), in solution, experiments have been performed with a shear apparatus as illustrated in FIG. 5. A computer-controlled syringe pump 40 delivers a specified amount of sample fluid containing CCVJ at a specific, accurate rate. The syringe pump 40 is fluidly coupled to a glass tube 42 with a flexible connecting tube 44. The fluid flows through the glass tube 42, which contains a fiber optic probe 46 at its center, permitting measurement of the CCVJ fluorescence emission in the vicinity of a fiber tip 48. The probe 46 is inserted into the system by a cannula 50 stuck through a gasket 52. Fluid is collected in a repository 54 connected to the system through a T-piece 56. This allows the syringe pump to refill as well as inject. The fiber optic probe 46 is connected to a fluorometer (not shown) for excitation light generation and emission detection.

Figure 6:
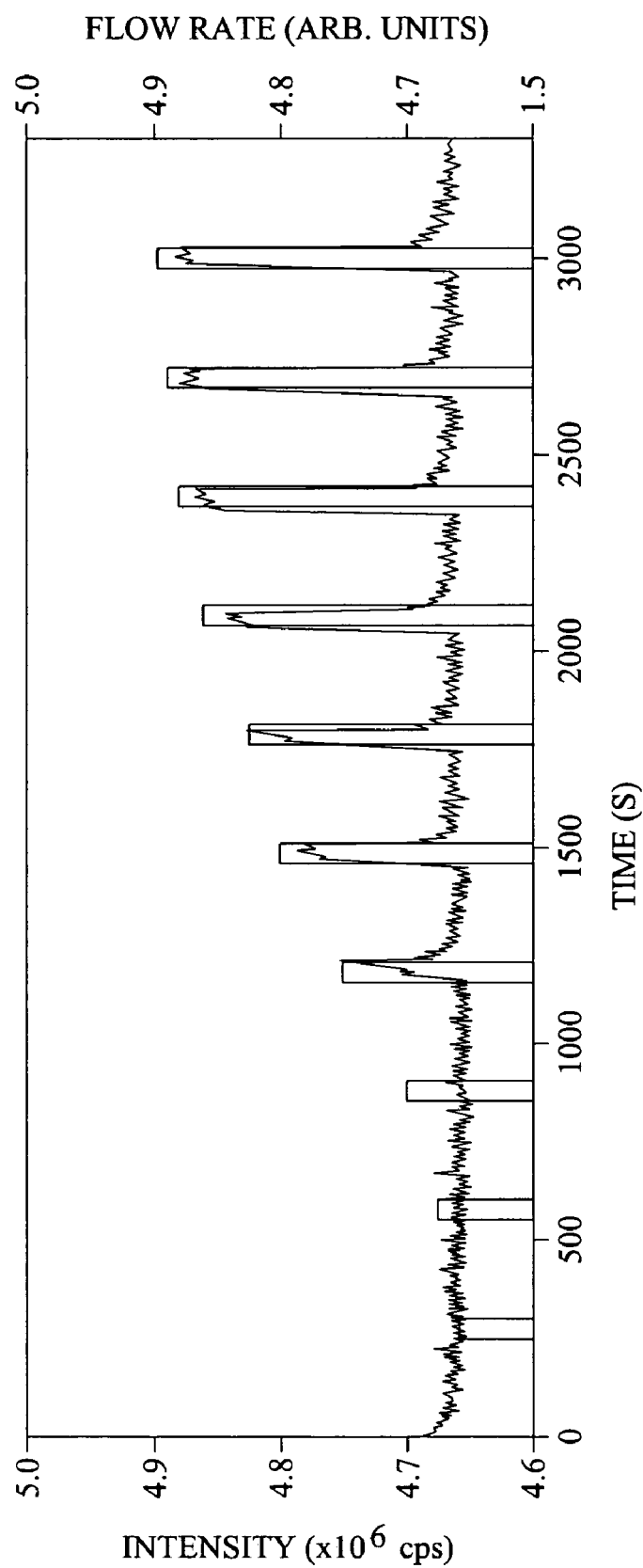
FIG. 6 is a timecourse graph of a typical shear stress experiment.

Fluids used to demonstrate this embodiment were water, aqueous colloid solutions, and mixtures of ethylene glycol and glycerol with 30 µM CCVJ in solution. A marked increase of the CCVJ emission intensity was observed with shear, followed by a recovery of the intensity baseline level upon cessation of shear. Higher flow rates led to higher emission intensities. A typical timecourse of a shear experiment is illustrated in FIG. 6. A solution of 15 µM CCVJ in ethylene glycol was exposed to increasing flow rates of 1 minute duration with 3 minutes of no flow in between. Emission intensity increases instantaneously with the onset of flow and returns to baseline level after flow cessation. Increased flow rates lead to higher intensities. Flow rates were 0.05, 0.1, 0.25, 0.5, 0.75, 1.0, 2.5, 5.0, 7.5, 9.0 ml/min. No intensity change was increased in a control system without any fluorescent dye and in a control system using fluorescein dye.

Two effects were observed. First, the intensity increase was independent of flow direction with the exception of a small deviation that may be explained by flow perturbation caused by the fiber. Second, at high shear rates intensity did not increase proportionally; rather there was a saturation effect likely caused by the quantum yield approaching unity.

Figure 7:
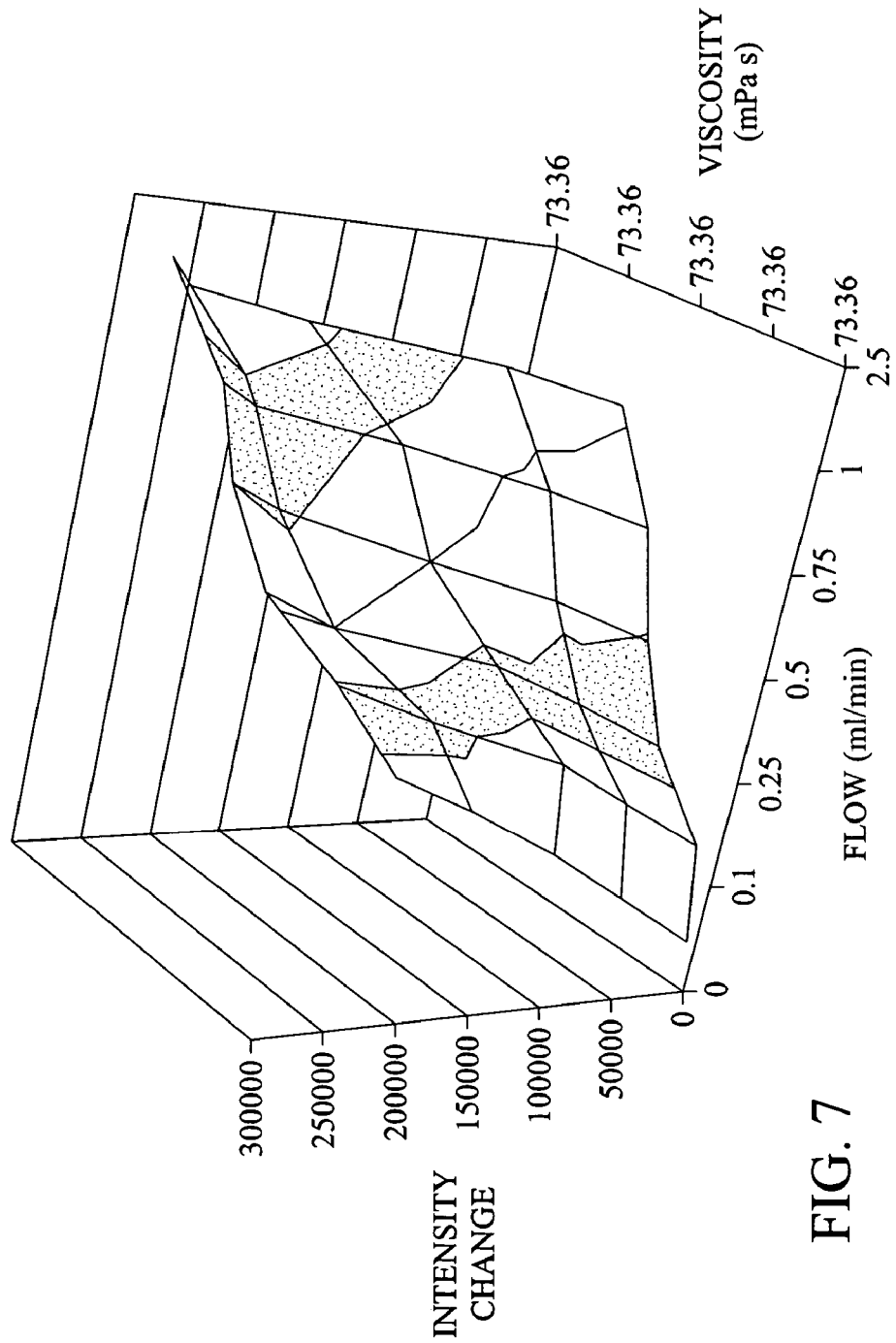
FIG. 7 is a graph illustrating that intensity is modulated by both viscosity and flow, indicating that shear stress rather than shear rate causes the intensity increase (axes are not drawn to scale.)

The proof that the sensor is sensitive to shear stress rather than shear rate was given by the observation of different fluids with different viscosities. If the hypothesis holds true, one would expect a similar increase of intensity with increases of flow and viscosity. If the hypothesis were false (i.e., the sensor reacts to flow only but not to shear stress), intensity increase would turn out to be independent from viscosity. Different mixtures of ethylene glycol and glycerol as well as ethylene glycol and methanol were used to modulate viscosity, and timecourse data such as described in FIG. 6 were obtained. The result is illustrated in FIG. 7. Clearly, both viscosity and flow modulate the intensity gain.

EXAMPLES

An exemplary in vitro analysis is useful in applications involving nanomachines, liquid chromatography and closed loop control of microfluidic machines. Nano-sized channels are used in such applications, and uniform shear stress of the channels is desirable, and minor deviations, such as those caused by occlusions, will alter the shear stress. Using molecular rotors to measure shear stress in these applications allows the channels to be checked for occlusions or other deviations as seen through fluorescence measurement.

For example, FIGS. 8A and 8B illustrates a rotor-based flow sensor element, designated generally at 58, in a closed-loop flow control system, designated generally at 60. One wall 62 of a flow channel 64, potentially a microchannel where the flow sensor element 58 is located, is covered with covalently bound molecular rotors. There is an optical window 66, which allows both excitation light 68 and emission light 70, which is flow-dependent, to pass. A light source (not shown) for providing the excitation light 68 is also provided, and may either be an external blue laser or light-emitting diode (LED) or similar source of blue light. Alternatively, it is also possible to integrate a small blue LED or semi-conductor laser, such as a vertical cavity surface emitting laser (VC-SEL), in the flow channel 64 itself, thus staying within the microscale range. Emission light 70 is directed through an emission filter 72 (to get rid of scattered blue light), and collected by a suitable sensor 74, such as a photomultiplier tube (PMT), or an avalanche photodiode (APD), the latter of which can be integrated on the microscale level.

The rotor-based flow sensor element 58 is disposed within the closed-loop flow control system 60, which is fluidly coupled to a reservoir 76, a MEMS pump 78, and a pump control 80. Flow is in the direction indicated by arrow 82. As flow increases, the rotor's fluorescence emission also increases. This is detected by the sensor 74 (PMT or APD) and converted into an electrical signal. Subtracting this signal from a setpoint signal provides the control voltage for the pump 78—increased flow leads to increased sensor voltage, which decreases the pump control voltage, in turn decreasing pump output until the setpoint is reached again.

The sensor of the instant applications may have in vivo applications as well. While the invention contemplates use of any solid-bound or dissolved rotor having a polar group, exemplary rotors include solid-bound polar rotors having one of the structures illustrated in FIGS. 1A through 1F, where R2 is one of a COOH, OH, $(CH_2O)_nCH_3$, and $O(CHOH)_n CH_2OH$ (the groups responsible for shear sensitivity), and could be adhered to a fiber optic tip or other solid surface. In this application, a catheterized fiber optic probe would be inserted into a subject blood vessel, acquiring shear data at the site of insertion. For example, when inserted into the ventricles of the heart or at arterial bifurcations, shear data would be collected at those sites. To differentiate between shear and viscosity, a pure viscosity sensor may include nonpolar groups (e.g., CN), while the shear sensor would include polar groups (e.g., COOH). R1 would preferably be used as a reference moiety, wherein one R1 group is preferably fluorescent but not viscosity-sensitive. Intensity could be accurately calibrated by computing a ratio of rotor fluorescence to a reference fluorescence.

Still another exemplary application of the sensor is measuring single bulk emission values, which are related to average shear stress, through fluoroscopy techniques. For example, one application includes a device similar to a pulse oxymeter, where bulk emission values are obtained percutaneously in blood vessels close to the skin. Rotors are dissolved in blood vessels close to the skin (in vivo) using rotor-labeled microspheres. Excitation light is then directed to those blood vessels, and emission light is measured with a detector placed close to the skin and subject vessel(s).

Experiments: Materials, Methods and Results

Instrumentation

Fluorescence measurements were performed on a Fluoromax-3 spectrophotometer equipped either with the standard four-sample cuvette holder, which includes temperature control and a magnetic stirrer, or with a custom fiberoptic attachment that was mounted inside the sample compartment. The fiberoptic attachment consisted of an SMA-connector with collimating lens; a dichroic shortpass mirror ($8_{50}$=465 nm) that allowed blue excitation light to pass from the excitation monochromator to the SMA adaptor, while reflecting green emission light into the emission monochromator; and an additional 475 nm longpass filter in the emission path. A multimode optical fiber with 0.48 numerical aperture and 600:m core was cut to expose the core on one end. A tip was formed by etching in 48% hydrofluoric acid for two to four hours. Capillary action between the silica core and the reflective layer around the core ("cladding") tapers the tip. The process was monitored visually with a 4× microscope objective until a fine point was observed. The other end of the fiber entered the fluorometer sample compartment through a curtain of blackout material and was attached to the SMA connector. With this instrumentation, the fiber acted as light guide for both excitation and emission light.

A shear apparatus was constructed from a glass pipette (2 ml volume, inner diameter 4 mm) attached to a side hole that was drilled into a small (30 ml) plastic container. The fiberoptic tip was guided into the pipette through a second hole on the opposite side to the pipette. The tip was placed at 20 mm distance from the end of the pipette in order to stay in a region of undisturbed flow. The fiber was then supported outside of the container to prevent lateral movement, and to center the tip with respect to the pipette. Silicone seals prevented leaking of the fluid.

Figure 9:
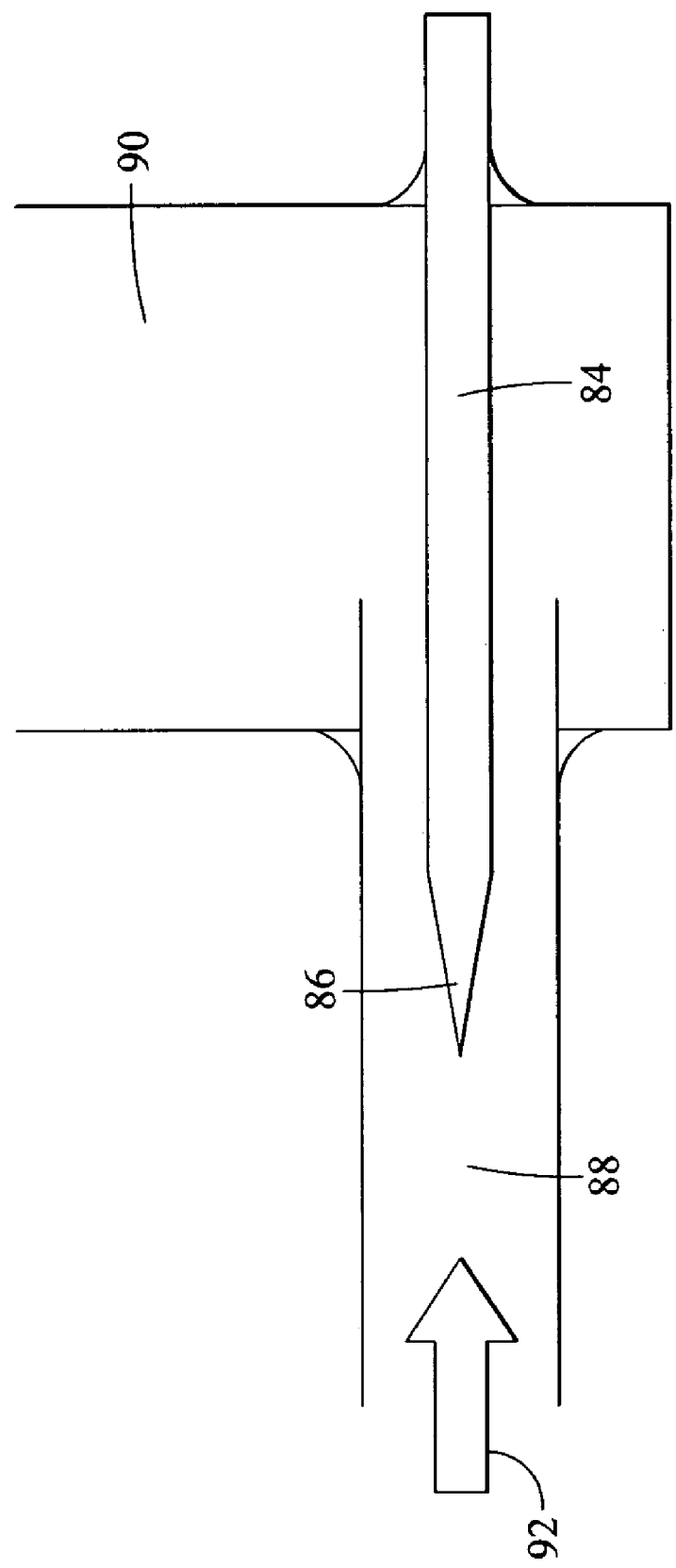
FIG. 9 is a schematic diagram illustrating a fiberoptic shear apparatus.

A sketch of the shear apparatus can be found in FIG. 9. The optical fiber 84 with an etched tip 86 was placed in the center of a glass pipette 88. A small plastic container 90 served as fluid repository and also held the pipette 88 and the fiber 84 in position. The tip 86 was inserted 20 mm upstream of the pipette 88 end to keep it in an undisturbed flow region. Flow 92 was applied to the far end of the pipette 88 with a syringe pump (not shown). The other end of the pipette 88 was connected to a computer-controlled syringe pump (not shown) to deliver defined flow rates and flow profiles.

Fluid Preparations

Figure 2B:
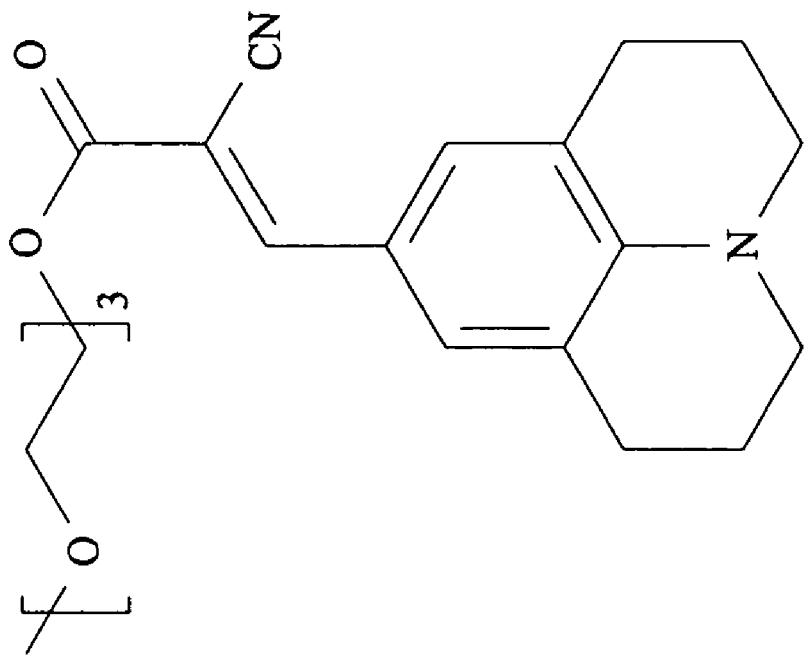
FIGS. 2A, 2B, 2C, 2D, 2E, 2F and 2G illustrate structures of seven exemplary molecular rotors.
Figure 2A:
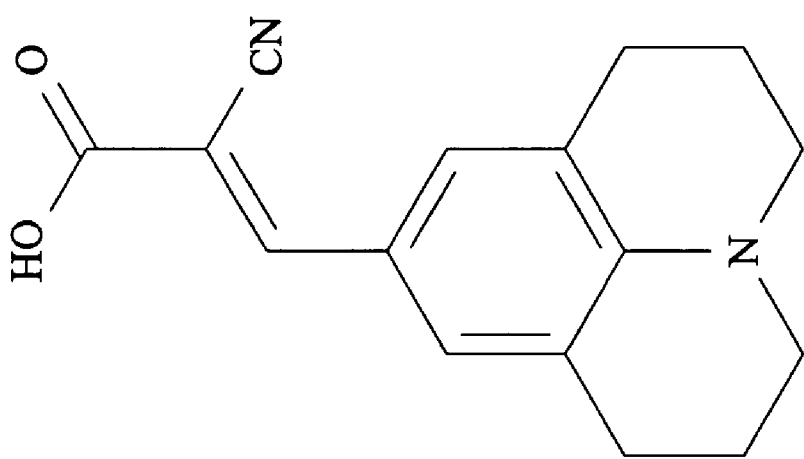
Figure 2D:
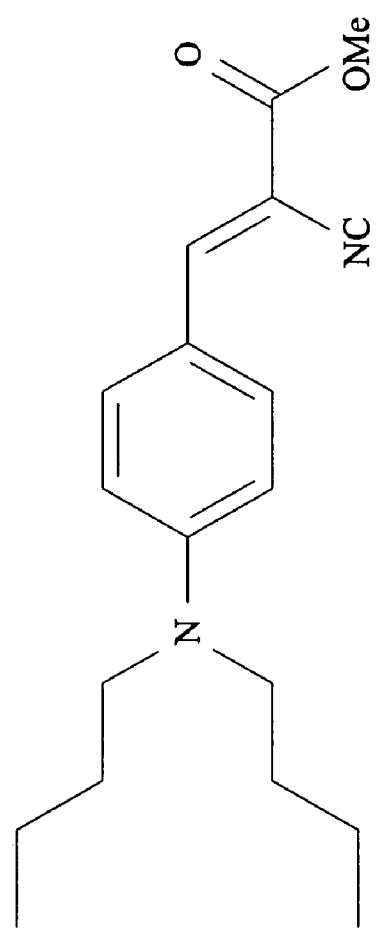
Figure 2C:
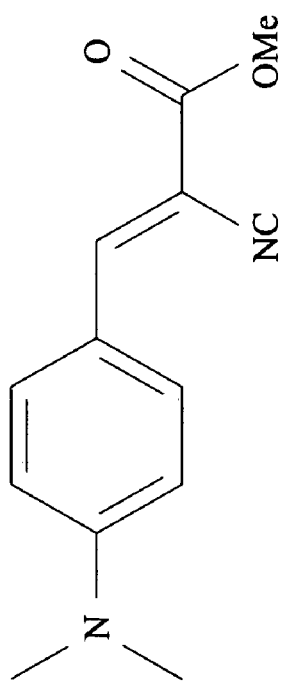
Figure 2G:
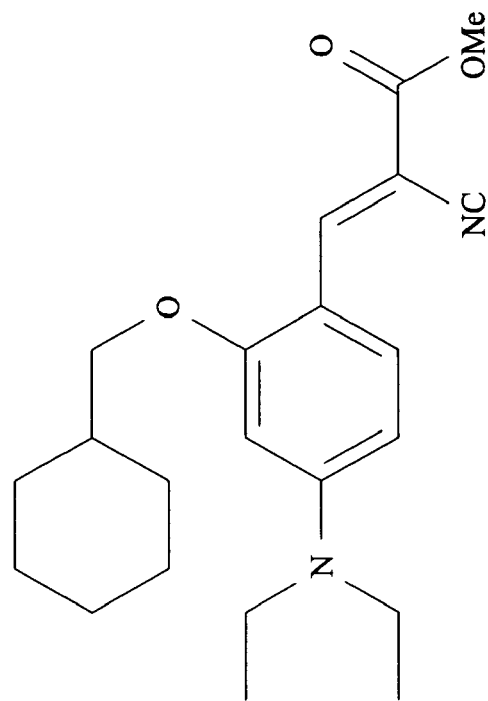
Figure 2E:
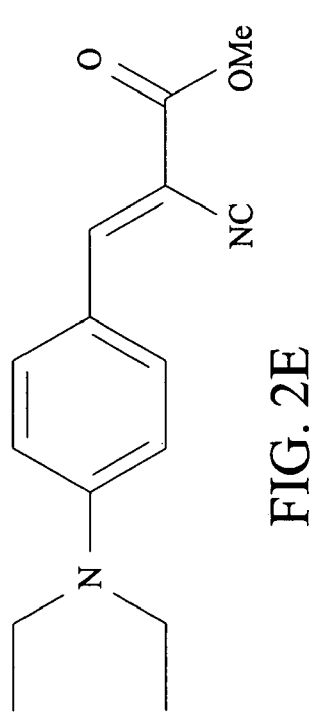
Figure 2F:
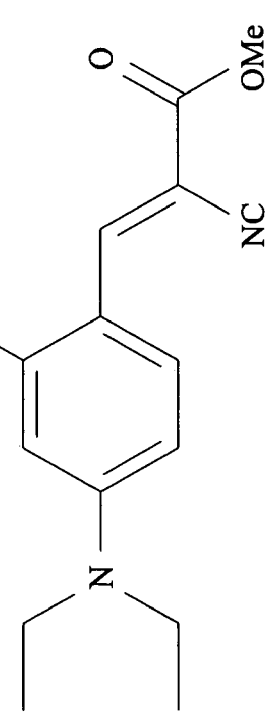

Three molecular rotors were examined: 9-(2,2-dicyanovinyl)-julolidine (DCVJ) and 9-(2-carboxy-2-cyanovinyl)-julolidine (CCVJ) and CCVJ-triethyleneglycol ester (CCVJ-TEG). FIGS. 2A and 2B show the chemical structures of the compounds. The difference is the presence of a functional group (COOH in the case of CCVJ and triethyleneglycol in the case of CCVJ-TEG) that defines solvent interaction, primarily water-solubility. Viscous fluids were prepared from mixtures of methanol, ethylene glycol and glycerol. Each of the mixtures was stained with one fluorescent molecular rotor at a concentration of 10 µM. Additional fluids were prepared with fluorescein at the same concentration. Fluorescein is not a molecular rotor and therefore serves as control.

Each of the fluids was filled into a 30 ml syringe that was placed on the syringe pump. The pipette was carefully filled to avoid air bubbles. Flow profiles were generated under computer control as follows: After obtaining the intensity baseline at no flow for 1 minute, flow was turned on for 30 seconds and paused for 1 minute, then turned on at the next higher level and so on, until a sequence of 0 ml/min, 0.05 ml/min, 0.1 ml/min, 0.25 ml/min, 0.5 ml/min, 0.75 ml/min, 1 ml/min, 2.5 ml/min, 5 ml/min, 7.5 ml/min, and 10 ml/min was completed, covering a flow range over a factor of 200. In the case of water, flow rates of 0.05 ml/min and 0.1 ml/min were omitted. Differences were computed from the average intensities over the 30 seconds of flow minus the average baseline intensity.

Statistical Analysis

Each experiment was performed in triplicate with the exception of the matrix experiments (intensity increase as a function of shear rate and viscosity), where experiments were repeated four times. Error bars show mean value±SD. In the stirrer experiments, the t-test was used to determine if averaged intensity during the stirring period was statistically different from averaged intensity before stirring. Flow-dependent intensity increase was computed by averaging emission intensity during the flow period and subtracting averaged intensity of the no-flow period before and after flow application. The resulting data (intensity increase $\Delta I$ over flow rate) were analyzed using the one-sample t-test to test whether $\Delta I$ was significantly different from zero for a specific flow rate. One-way ANOVA was performed on the complete data set. A post-test for linear trend was performed to determine the significance of the overall increasing trend, while Bonferroni's multiple comparison test provided information on the difference of neighboring $\Delta I$. Statistical analysis was performed using Graphpad Prism version 4.00. Significance was assumed at $p<0.05$.

Results

Basic Behavior of Molecular Rotors in Sheared Fluids

Figure 10:
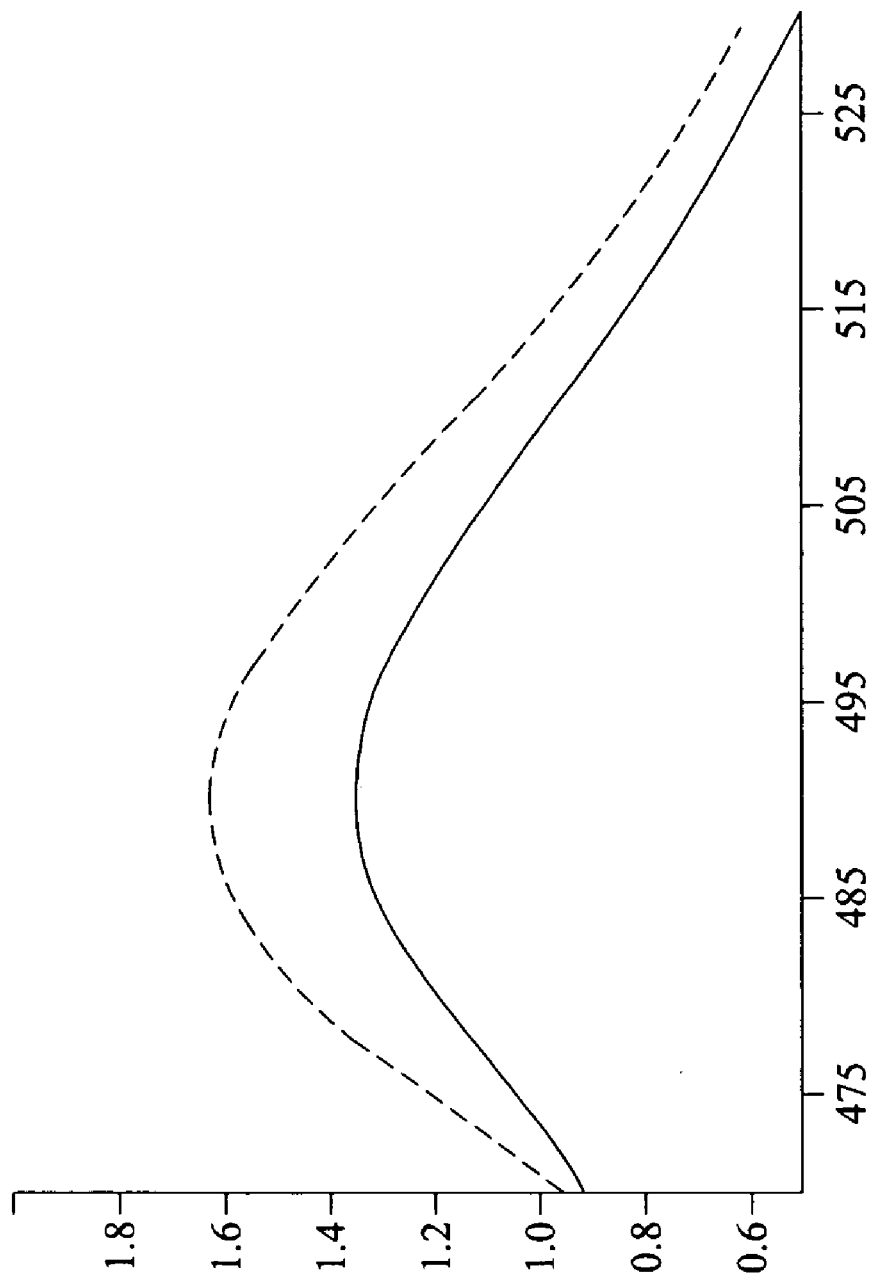
FIG. 10 is a graph illustrating a comparison of the emission spectra of CCVJ in a cuvette without fluid motion and when stirred.
Figure 11B:
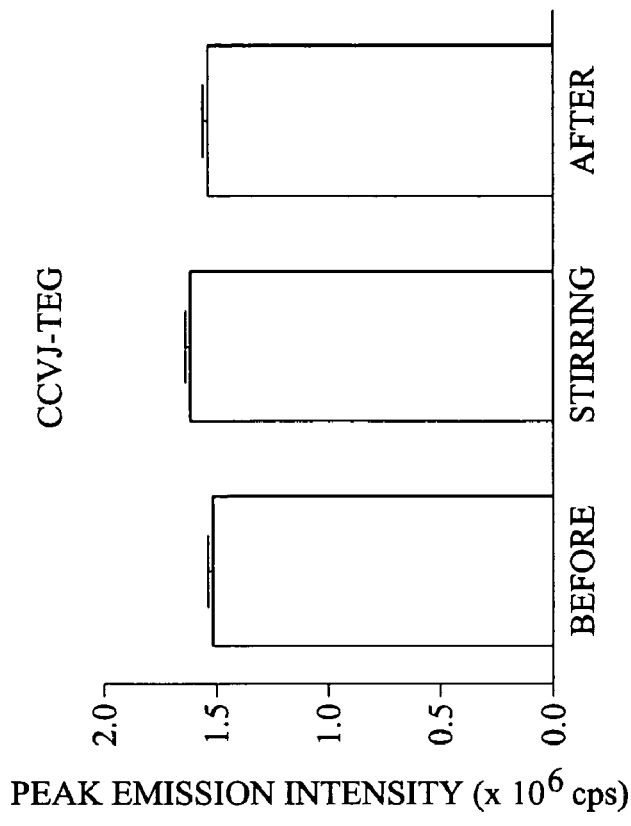
FIGS. 11A-11D are graphs illustrating 10 µM CCVJ in ethylene glycol in a fluorometer cuvette before the stirrer was activated, during, and after stirring.
Figure 11A:
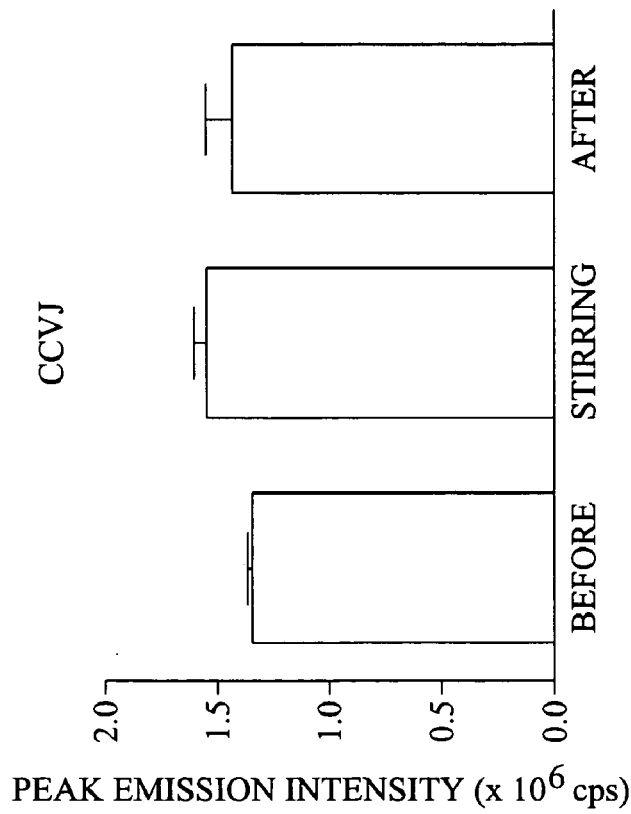
Figure 11D:
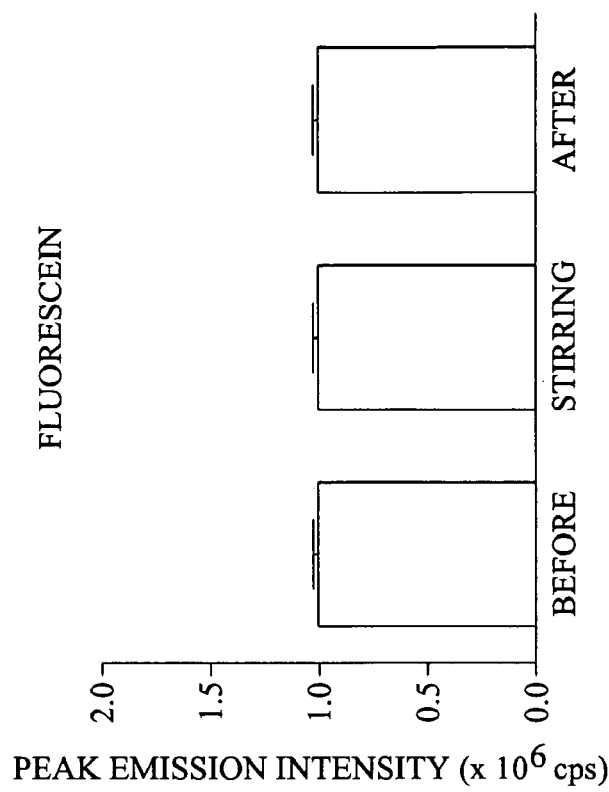
Figure 11C:
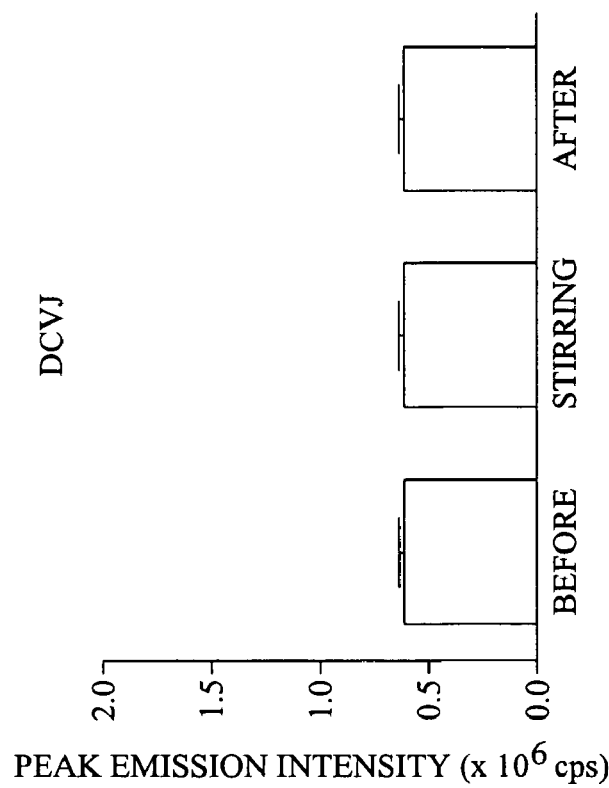

Molecular rotors featuring a functional group, CCVJ and CCVJ-TEG, showed a marked increase in emission intensity when the fluids were sheared. FIG. 10 allows the comparison of the emission spectra of CCVJ in a cuvette without fluid motion and when stirred. A 20% increase in peak emission intensity was observed. A similar, but lower (7%), increase was observed with CCVJ-TEG. In three independent experiments for each dye, this increase was statistically significant ($p<0.05$). Neither fluorescein nor DCVJ exhibited any increase in emission intensity (FIGS. 11A-11D) under the same conditions. In FIGS. 11A-11D, slow stirring increases both CCVJ and CCVJ-TEG intensity significantly (t-test, $p<0.05$) over unstirred control. Two control dyes, DCVJ and fluorescein do not show this increase (t-test, n.s.).

Figure 12:
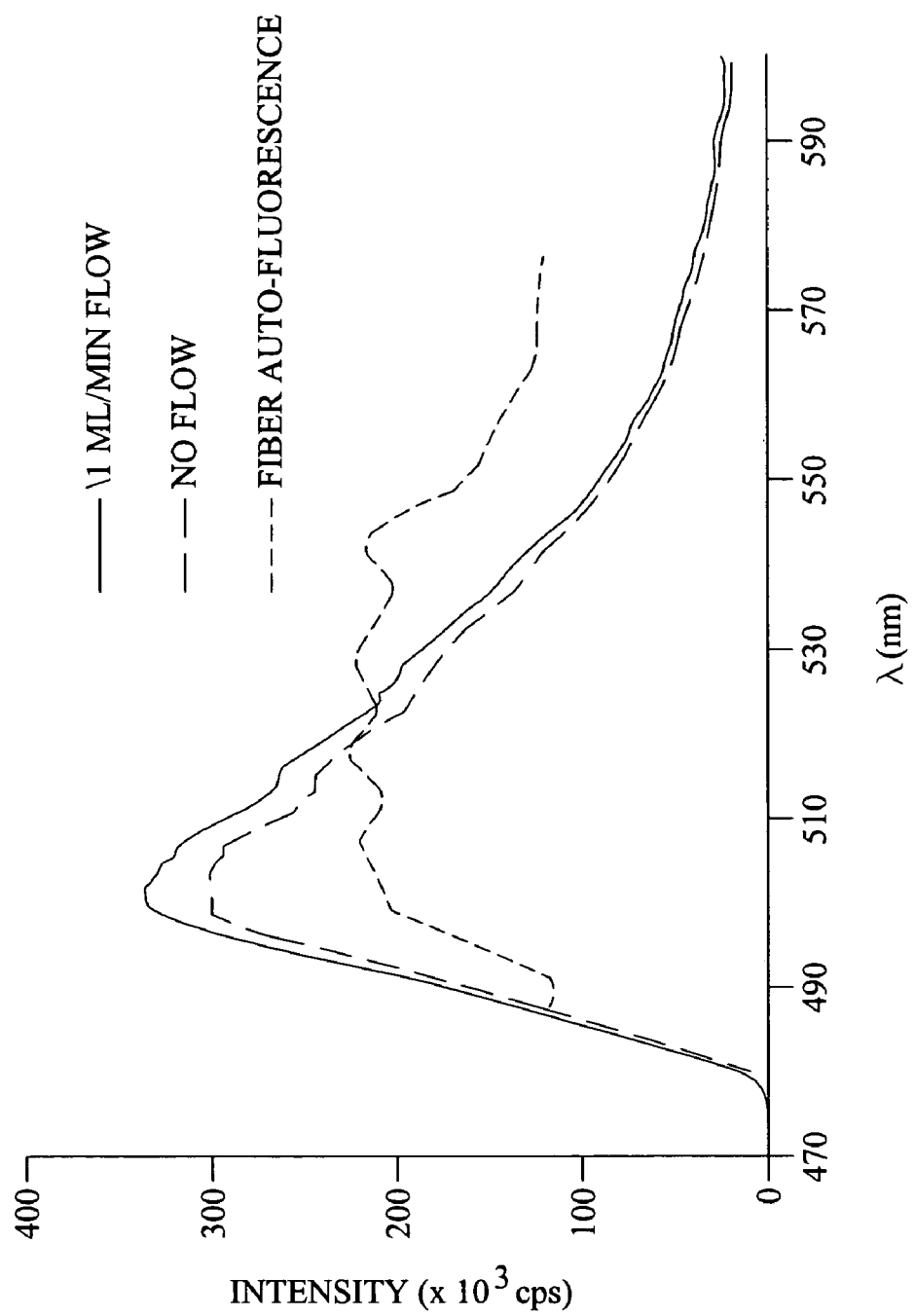
FIG. 12 is a graph illustrating background-corrected fluorescence emission spectrum of 10 µM CCVJ in ethylene glycol without flow and at 1 ml/min flow.

In the fiberoptic-based flow apparatus, a similar intensity increase was observed. Emission spectra of 10 µM CCVJ in ethylene glycol in the presence and absence of flow can be seen in FIG. 12. Spectroscopy indicates that emission intensity increases with flow. No spectral shifts were observed. The background signal (fiber immersed in ethylene glycol without dye) that was subtracted from the dye spectra is shown as grey dotted line. Peak intensity increased by about 10% under the application of 1 ml/min flow, which corresponds to a fluid velocity of 2.7 mm/s in the center of the tube. This increased emission intensity was not observed in three control fluids, (1) ethylene glycol without any fluorescent dye, (2) ethylene glycol with 10 µM fluorescein, which is not a molecular rotor, and (3) ethylene glycol with 10 µM DCVJ, a hydrophobic molecular rotor without hydrophilic functional groups.

Figure 13:
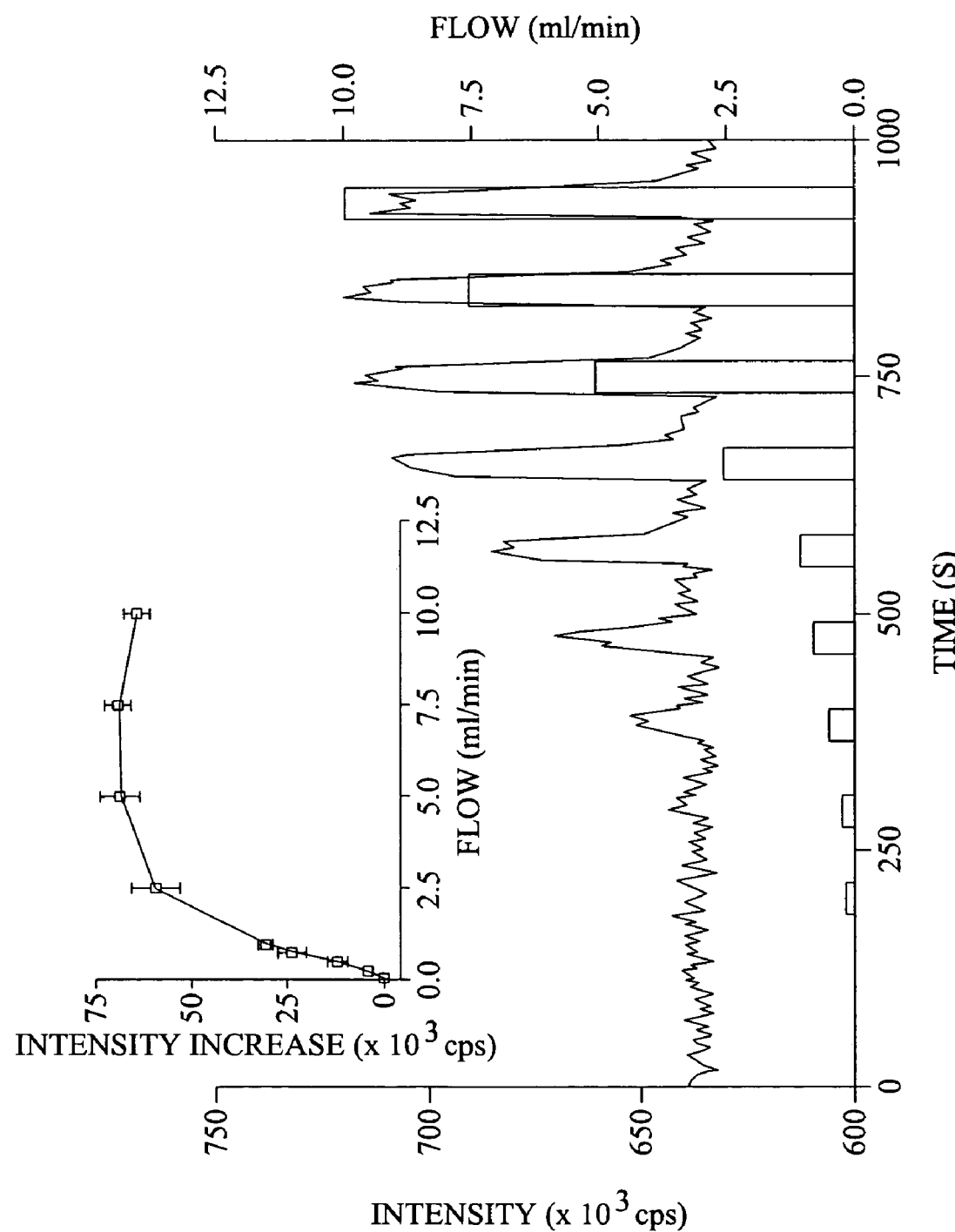
FIG. 13 is a graph illustrating a representative timecourse experiment where emission intensity of 10 µM CCVJ in ethylene glycol was monitored at fixed excitation and emission wavelengths.
Figure 14:
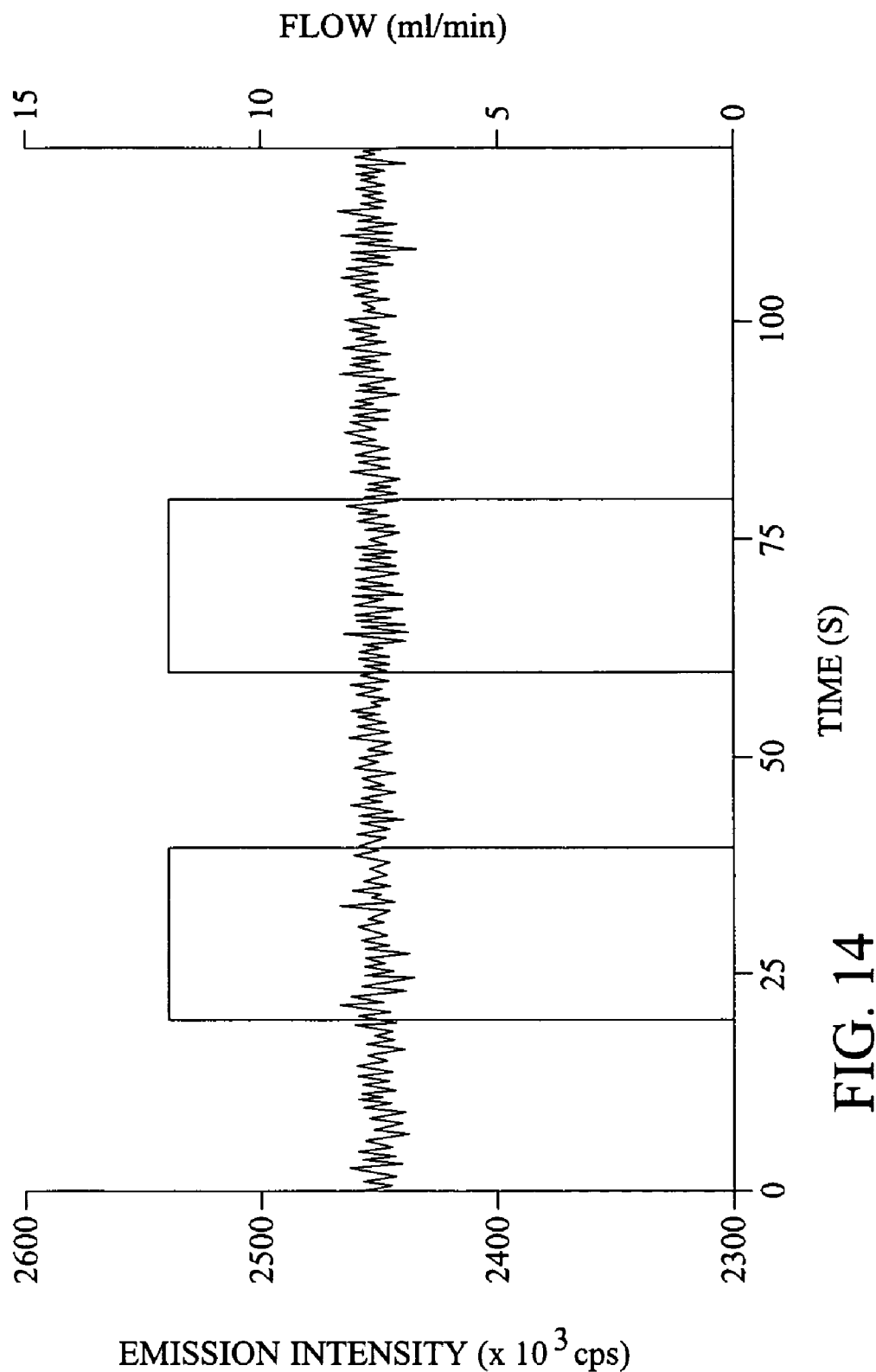
FIG. 14 is a graph illustrating a negative control timecourse experiment using 10 µM 9-(2,2-dicyanovinyl)-julolidine (DCVJ) in ethylene glycol.
Figure 15:
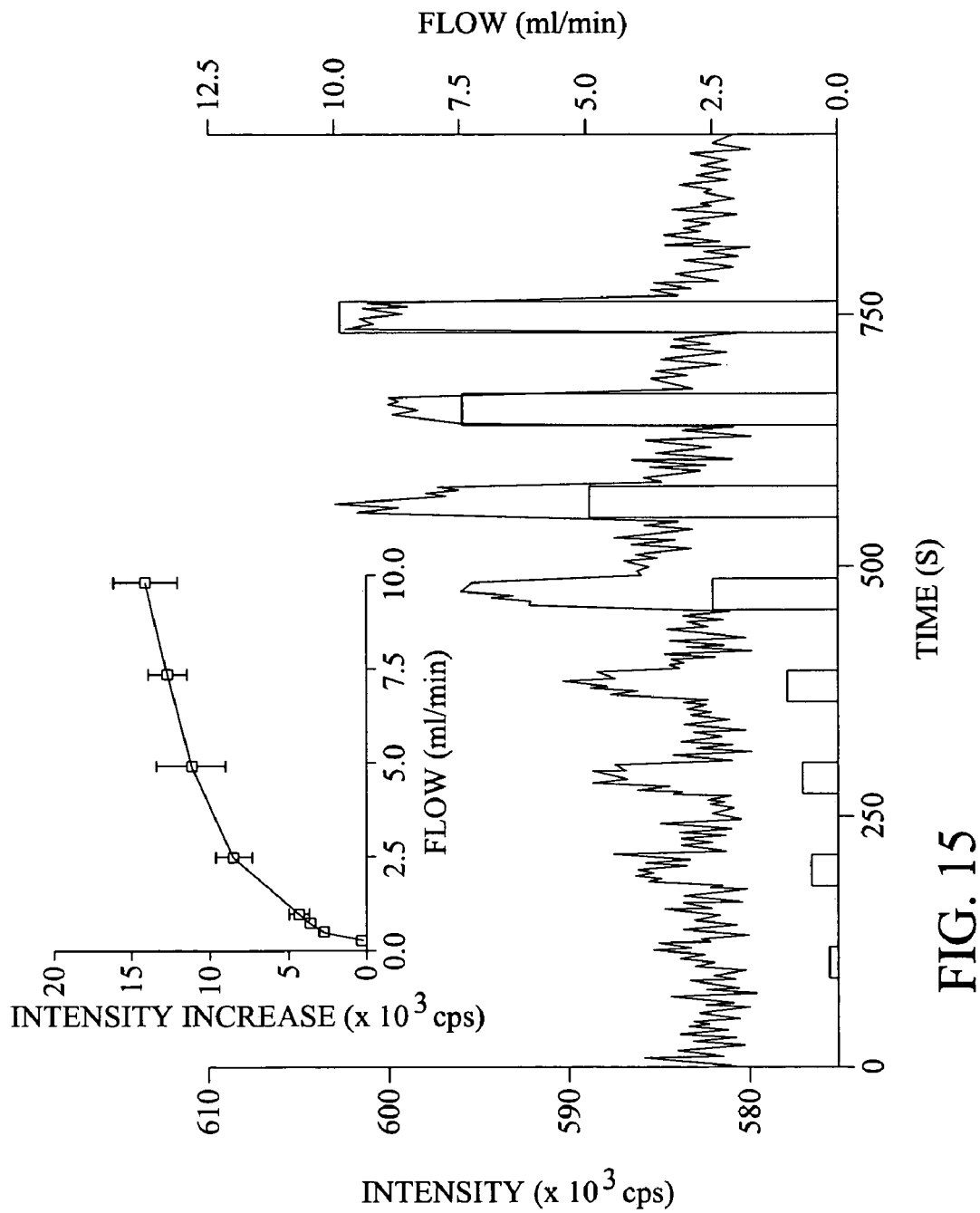
FIG. 15 is a graph illustrating a representative timecourse experiment where emission intensity of 10 µM CCVJ in water was monitored at fixed excitation and emission wavelengths.

Intensity increase was higher with higher flow rates in a dose-response fashion. FIG. 13 shows a representative timecourse of emission intensity in response to flow. It can be seen that a statistically significant increase over the no-flow intensity level is achieved at flow rates as low as 0.25 ml/min. For flow rates of 0.05 ml/min and 0.1 ml/min, $\Delta I$ was not significantly different from zero. An overall linear trend of $\Delta I$ was observed with increasing flow rates ($p<0.0001$). $\Delta I$ at flow rates of 5 ml/min, 7.5 ml/min, and 10 ml/min were not statistically different from each other. FIG. 14 is provided to illustrate a negative control, and shows a timecourse experiment with DCVJ in ethylene glycol. As opposed to both CCVJ and CCVJ-TEG, no changes in intensity were observed, in spite of relatively high flow rates. No increase in emission intensity was observed. The water-soluble dyes CCVJ and CCVJ-TEG were also tested in water. While CCVJ-TEG failed to exhibit an intensity increase under shear in water, the effect could clearly be observed with CCVJ (FIG. 15). Flow was increased from 0.25 ml/min to 10 ml/min. Inset shows the averaged intensity during periods of flow as a function of the applied flow rate. Similar to the experiment in ethylene glycol (FIG. 13), application of flow led to an increased emission intensity in a dose-response fashion. Higher flow rates than 5 ml/min did not lead to significantly higher emission intensities. In FIG. 13, flow was increased over a wide range (factor of 100). Inset shows the averaged intensity over baseline during periods of flow as a function of the applied flow rate. Application of flow leads to an increased emission intensity in a dose-response fashion, but no significant increase was seen below 0.05 and 0.1 ml/min, and an apparent saturation effect (no further increase of intensity) becomes visible above 5 ml/min. The apparent (and nonsignificant) decrease of intensity at 10 ml/min may be attributed to unstable flow conditions. Consistent with the lower viscosity of water relative to ethylene glycol, the intensity increase was markedly lower. No measurable intensity increase was observed with flow rates of 0.1 ml/min and below. At flow rates of 0.5 ml/min and above, $\Delta I$ was significantly different from zero. In addition, a significant linear trend of $\Delta I$ over flow was observed ($p<0.0001$).

Differentiation Between Shear Rate and Shear Stress

Figure 16B:
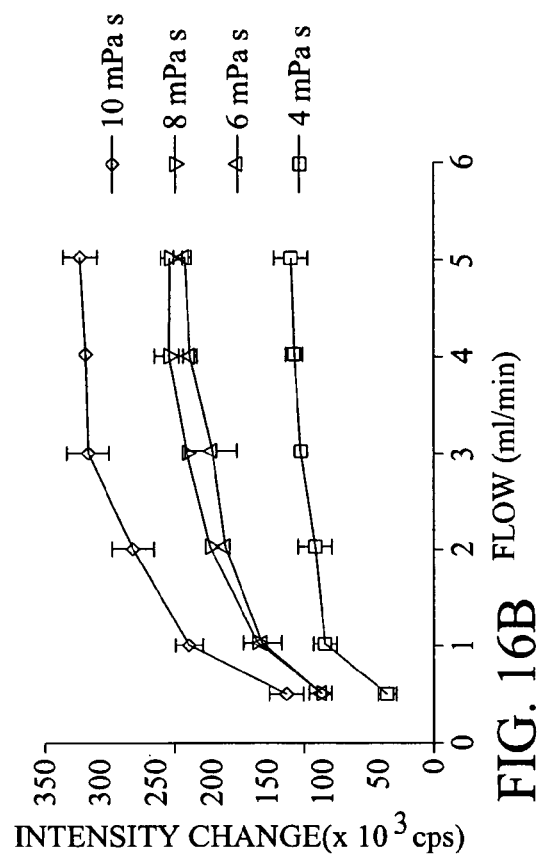
FIGS. 16A and 16B are graphs illustrating a matrix experiment where intensity increase was observed at different flow rates in fluids of different viscosities (mixtures of ethylene glycol and glycerol)
Figure 16A:
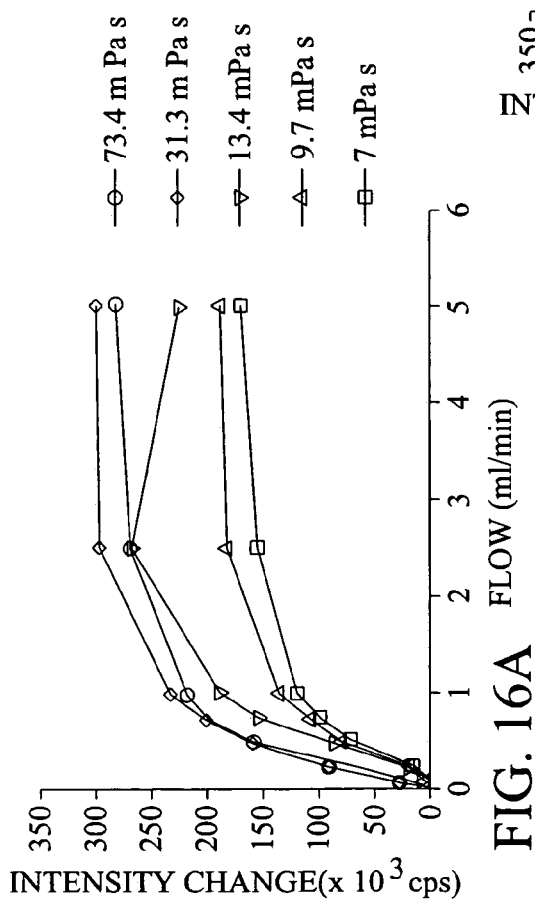

In order to differentiate between shear rate and shear stress effects, timecourse experiments were repeated with the same flow profile, but with fluids of different viscosity. It can be seen in FIGS. 16A and 16B that intensity increases occur with both increased flow and increased viscosity. Shown are the dyes CCVJ (16A) in a single experiment and CCVJ-TEG (16B) as means and SD of four experiments. Intensity increase can be seen with both flow and viscosity, indicating that the effect is based on shear stress rather than shear rate. This effect was observed with both CCVJ and CCVJ-TEG. In both cases, the response (differential intensity increase) was higher at low flow rates and low viscosities.

Possible Applications as Flow and Shear Sensors

Figure 17:
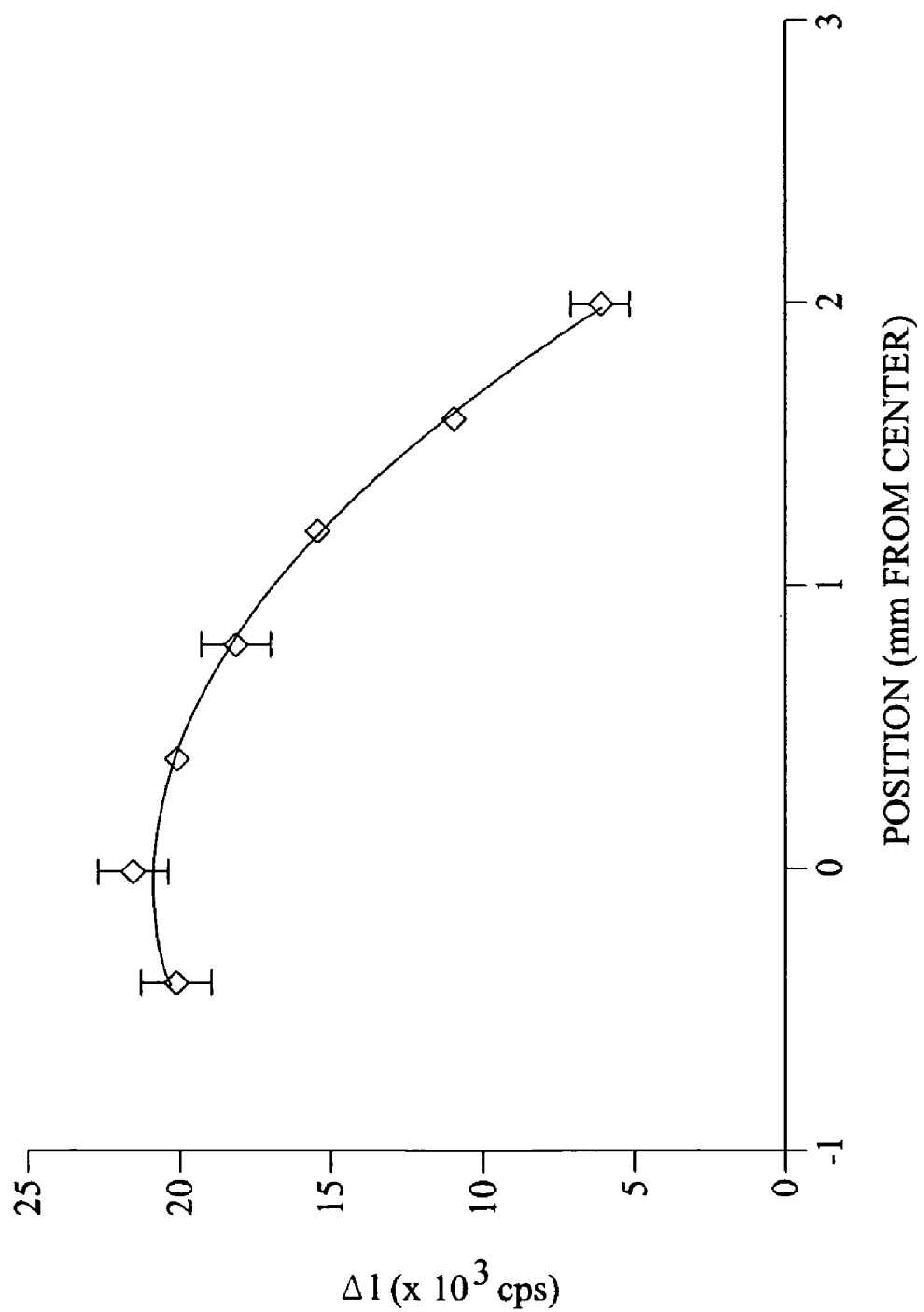
FIG. 17 is a graph illustrating an intensity increase caused by constant flow but with varying radial position of the fiber tip in a cylindrical tube.

Flow velocity in a cylindrical tube exhibits a parabolic profile v(r) following Equation 1, $$v(r) = V_{max} \cdot \left(1 - \frac{r^2}{R^2}\right)$$

where $V_{max}$ is the flow velocity in the center of the tube, and R is the tube radius. By changing the position of the fiber tip relative to the wall, the tip was exposed to different flow velocities. As the tip was placed closer to the wall, a less pronounced intensity increase was observed (FIG. 17). As can be seen in FIG. 17, the intensity increase follows closely the expected parabolic profile with a maximum in the tube center and a minimum close to the tube wall ($R^2=0.98$). Shown is means±SD of three experiments. Maximum intensity increase was seen in the tube center, with a marked reduction towards the tube wall. A parabolic profile, following the flow velocity equation in a cylinder (equation 1), shows an excellent fit into the data. Deviation of the data values from the model were not significant (runs test, p=0.84), indicating that the parabolic model is applicable to describe the data.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. A method for measuring local flow or shear stress comprising:
   exposing a solid surface having molecular rotors attached thereto to a fluid having a shear stress to be measured; and
   measuring fluorescence emission signal intensity to make conclusions about shear stress values.

2. The method of claim 1 further comprising a first step of attaching molecular rotors to the solid surface.

3. The method of claim 1 wherein the molecular rotors have a structure

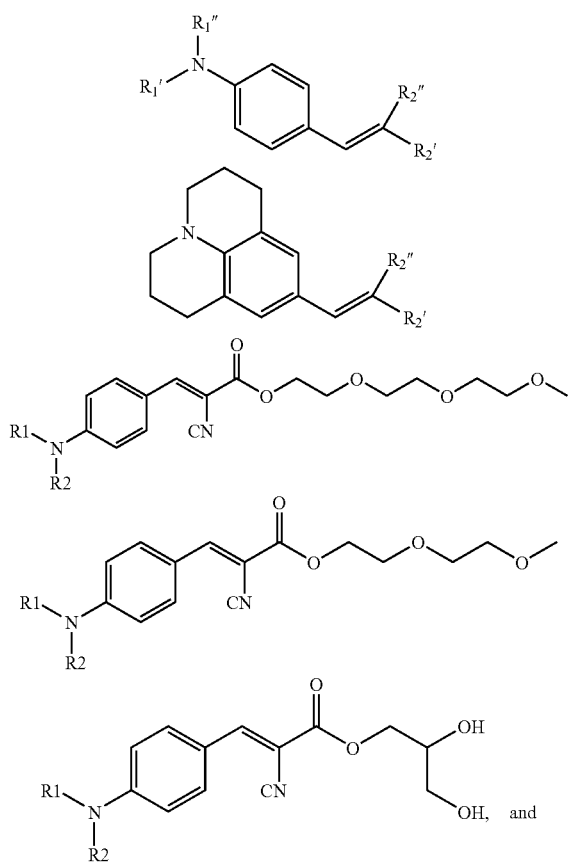

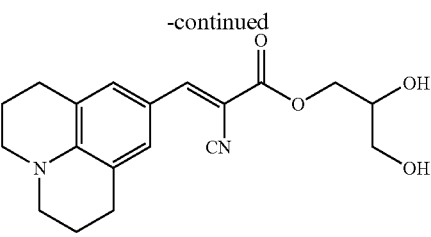

where at least one of an R2, R2' and R2" each act as both electron acceptors and polar groups.

4. The method of claim 3 wherein at least one of the R2' and the R2" include one of the group consisting of COOH, OH, $(CH_2O)_nCH_3$, and $O(CHOH)_nCH_2OH$.

5. The method of claim 3 wherein one of the R2' and the R2" include one of the group consisting of COOH, OH, $(CH_2O)_nCH_3$, and $O(CHOH)_nCH_2OH$, and the other of the R2' and R2" function as either a recognition unit or as an attachment unit.

6. The method of claim 1 wherein the molecular rotors comprise one of 9-(2-carboxy-2-cyanovinyl)-julolidine (CCVJ); 9-(2-carboxy-2-cyanovinyl)-julolidine triethyleneglycol ester (CCJV-TEG); 2-Cyano-3-(4-dimethylamino-phenyl)-acrylic acid methyl ester (DMCJ); 2-Cyano-3-(4-dibutylamino-phenyl)-acrylic acid methyl ester (SC1-20A); 2-Cyano-3-(4-diethylamino-phenyl)-acrylic acid methyl ester (SC1-40B); 2-Cyano-3-(4-diethylamino-2-pentyloxy-phenyl)-acrylic acid methyl ester (SC1-30B); and 2-Cyano-3-(2-cyclohexylmethoxy-4-diethylamino-phenyl)-acrylic acid methyl ester (SC1-31 B).

7. The method of claim 1 wherein the solid surface is composed of one of quartz, polystyrene and silicate glass.

8. The method of claim 1 wherein the solid surface is a tip of a fiber optic probe.

9. The method of claim 8 wherein the step of exposing the solid surface comprises inserting the tip of the fiber optic probe into the fluid.

10. The method of claim 8 further comprising catheterizing the tip of the fiber optic probe for in vivo insertion.

11. The method of claim 1 wherein the solid surface is at least one internal wall of a glass receptacle.

12. The method of claim 1 further comprising calibrating signal intensity by computing a ratio of rotor fluorescence value to a reference fluorescence value.

13. A shear stress sensor for in vivo and in vitro measurement of viscosity comprising:
   a solid surface; and
   fluorescent molecular rotors bound to said solid surface, said molecular rotors being of the type that include a hydrophilic head group and that emit fluorescence when intramolecular rotation is inhibited.

14. The sensor of claim 13 wherein said solid surface comprises a pre-functionalized surface configured for attaching molecular rotors.

15. The sensor of claim 13 wherein said solid surface is a glass surface composed of one of quartz, polystyrene and silicate glass.

16. The sensor of claim 13 wherein said solid surface comprises a tip of a fiber optic probe.

17. The sensor of claim 16 wherein said tip is configured for in vivo insertion into blood vessels.

18. The sensor of claim 13 wherein said solid surface comprises at least one internal wall of a glass cuvette.

19. The sensor of claim 18 wherein said glass cuvette is configured to receive a fluid having a shear stress to be measured.

20. The sensor of claim 13 wherein said molecular rotors have a structure

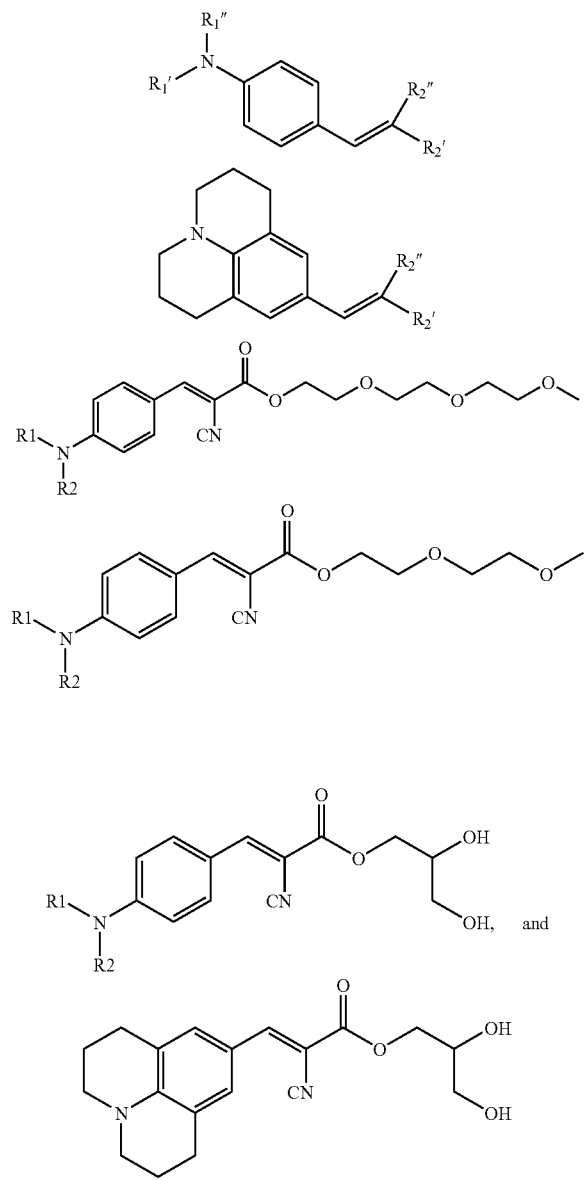

where at least one of R2' and R2" each act as both electron acceptors and polar groups.

21. The sensor of claim 13 wherein at least one of the R2' and the R2" include one of the group consisting of COOH, OH, $(CH_2O)_nCH_3$, and $O(CHOH)_nCH_2OH$.

22. The sensor of claim 13 wherein one of the R2' and the R2" include one of the group consisting of COOH, OH, $(CH_2O)_nCH_3$, and $O(CHOH)_nCH_2OH$, and the other of the R2' and R2" function as either a recognition unit or as an attachment unit.

23. The sensor of claim 13 wherein the molecular rotors comprise one of -9-(2-carboxy-2-cyanovinyl)-julolidine (CCVJ); 9-(2-carboxy-2-cyanovinyl)-julolidine triethyleneglycol ester (CCJV-TEG); 2-Cyano-3 -(4-dimethylamino-phenyl)-acrylic acid methyl ester (DMCJ); 2-Cyano-3-(4-dibutylamino-phenyl)-acrylic acid methyl ester (SC1-20A); 2-Cyano-3-(4-diethylamino-phenyl)-acrylic acid methyl ester (SC1-40B); 2-Cyano-3-(4-diethylamino-2-pentyloxy-phenyl)-acrylic acid methyl ester (SC1-30B); and 2-Cyano-3-(2-cyclohexylmethoxy-4-diethylamino-phenyl)-acrylic acid methyl ester (SC1-31B).

24. A method of measuring local shear stress values comprising:
    providing a sample;
    dissolving molecular rotors in the sample;
    exciting, by rotating an exciter-detector system around the sample, the the molecular rotors; and
    acquiring an emission profile.

25. The method of claim 24 wherein the step of acquiring an emission profile comprises coupling the sample to one of a CCD camera or a circular detector system.

26. The method of claim 25 further comprising filtering excitation light to prevent excitation light from reaching the CCD camera.

27. A method of measuring local shear stress values comprising:
    providing a sample;
    dissolving molecular rotors in the sample;
    exciting the molecular rotors;
    acquiring an emission profile; and
    calculating shear stress values based on the emission profile.

28. A method of measuring local shear stress values comprising:
    providing a sample;
    dissolving molecular rotors in the sample;
    exciting the molecular rotors;
    acquiring an emission profile; and
    measuring bulk emission values using fluoroscopy to calculate shear stress values.

29. The method of claim 28 further comprising dissolving rotor-labeled microspheres in the sample.

* * * * *